US010058554B2

(12) United States Patent
Luk et al.

(10) Patent No.: US 10,058,554 B2
(45) Date of Patent: *Aug. 28, 2018

(54) SUSTAINED RELEASE SMALL MOLECULE DRUG FORMULATION

(71) Applicant: INDIVIOR UK LIMITED, Slough (GB)

(72) Inventors: Andrew S. Luk, Castro Valley, CA (US); Gunjan H. Junnarkar, Palo Alto, CA (US); Guohua Chen, Sunnyvale, CA (US)

(73) Assignee: Indivior UK Limited, Slough, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/422,626

(22) Filed: Feb. 2, 2017

(65) Prior Publication Data

US 2017/0239252 A1 Aug. 24, 2017

Related U.S. Application Data

(63) Continuation of application No. 14/701,173, filed on Apr. 30, 2015, now Pat. No. 9,597,402, which is a continuation of application No. 13/790,930, filed on Mar. 8, 2013, now Pat. No. 9,044,450, which is a continuation of application No. 11/535,398, filed on Sep. 26, 2006, now Pat. No. 8,852,638.

(60) Provisional application No. 60/722,845, filed on Sep. 30, 2005.

(51) Int. Cl.
| A61K 9/14 | (2006.01) |
| A61K 31/519 | (2006.01) |
| A61K 9/06 | (2006.01) |
| A61K 9/16 | (2006.01) |
| A61K 9/00 | (2006.01) |
| A61K 51/12 | (2006.01) |

(52) U.S. Cl.
CPC .......... *A61K 31/519* (2013.01); *A61K 9/0024* (2013.01); *A61K 9/06* (2013.01); *A61K 9/1617* (2013.01); *A61K 9/1647* (2013.01); *A61K 51/1213* (2013.01)

(58) Field of Classification Search
None
See application file for complete search history.

(56) References Cited

U.S. PATENT DOCUMENTS

| 3,466,362 A | 9/1969 | Klaui et al. |
| 4,530,840 A | 7/1985 | Tice et al. |
| 4,534,974 A | 8/1985 | Kim |
| 4,573,995 A | 3/1986 | Chen et al. |
| 4,622,219 A | 11/1986 | Haynes |
| 4,626,539 A | 12/1986 | Aungst et al. |
| 4,725,442 A | 2/1988 | Haynes |
| 4,755,389 A | 7/1988 | Jones et al. |
| 4,767,628 A | 8/1988 | Hutchinson |
| 4,784,855 A | 11/1988 | Yamashita et al. |
| 4,804,663 A | 2/1989 | Kennis et al. |
| 4,891,225 A | 1/1990 | Langer |
| 4,906,474 A | 3/1990 | Langer |
| 4,938,763 A | 7/1990 | Dunn et al. |
| 4,957,744 A | 9/1990 | Della Valle et al. |
| 5,008,110 A | 4/1991 | Benecke et al. |
| 5,026,556 A | 6/1991 | Drust et al. |
| 5,069,909 A | 12/1991 | Sharma et al. |
| 5,096,715 A | 3/1992 | Sinclair |
| 5,149,543 A | 9/1992 | Cohen et al. |
| 5,173,304 A | 12/1992 | Lohner et al. |
| 5,278,201 A | 1/1994 | Dunn et al. |
| 5,324,519 A | 6/1994 | Dunn et al. |
| 5,453,425 A | 9/1995 | Francois et al. |
| 5,534,269 A | 7/1996 | Igari et al. |
| 5,612,346 A | 3/1997 | Mesens et al. |
| 5,616,587 A | 4/1997 | Francois et al. |
| 5,643,605 A | 7/1997 | Cleland et al. |
| 5,648,093 A | 7/1997 | Gole et al. |
| 5,656,299 A | 8/1997 | Kino et al. |
| 5,688,801 A | 11/1997 | Mesens et al. |
| 5,702,716 A | 12/1997 | Dunn et al. |
| 5,723,467 A | 3/1998 | Mesens et al. |
| 5,744,153 A | 4/1998 | Yewey et al. |
| 5,747,058 A | 5/1998 | Tipton et al. |
| 5,770,231 A | 6/1998 | Mesens et al. |
| 5,780,044 A | 7/1998 | Yewey et al. |
| 5,792,477 A | 8/1998 | Rickey |
| 5,871,778 A | 2/1999 | Kino |
| 5,916,598 A | 6/1999 | Rickey et al. |
| 5,945,115 A | 8/1999 | Dunn et al. |
| 5,965,168 A | 10/1999 | Mesens et al. |
| 5,968,542 A | 10/1999 | Tipton |
| 5,990,194 A | 11/1999 | Dunn et al. |
| 6,004,969 A | 12/1999 | Hu |
| 6,110,503 A | 8/2000 | Rickey et al. |
| 6,110,921 A | 9/2000 | Mesens et al. |
| 6,120,789 A | 9/2000 | Dunn |
| 6,130,200 A | 10/2000 | Brodbeck et al. |
| 6,143,314 A | 11/2000 | Chandrashekar et al. |

(Continued)

FOREIGN PATENT DOCUMENTS

| EP | 0 368 409 A2 | 5/1990 |
| EP | 0 368 409 A3 | 5/1990 |

(Continued)

OTHER PUBLICATIONS

Extracts from European Pharmacopoeia, 5$^{th}$ Ed., Jun. 15, 2004. pp. 5-7, 2374-2376.

(Continued)

*Primary Examiner* — James W Rogers
(74) *Attorney, Agent, or Firm* — Mintz Levin Cohn Ferris Glovsky and Popeo, P.C.

(57) ABSTRACT

An injectable depot formulation includes a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

20 Claims, 2 Drawing Sheets

(56) References Cited

U.S. PATENT DOCUMENTS

| | | |
|---|---|---|
| 6,194,006 B1 | 2/2001 | Lyons |
| 6,224,905 B1 | 5/2001 | Lawrence et al. |
| 6,261,583 B1 | 7/2001 | Dunn et al. |
| 6,264,987 B1 | 7/2001 | Wright et al. |
| 6,284,274 B1 | 9/2001 | Merrill et al. |
| 6,290,983 B1 | 9/2001 | Rickey et al. |
| 6,291,013 B1 | 9/2001 | Gibson et al. |
| 6,294,192 B1 | 9/2001 | Patel et al. |
| 6,303,137 B1 | 10/2001 | Dittgen et al. |
| 6,331,311 B1 | 12/2001 | Brodbeck et al. |
| 6,355,657 B1 | 3/2002 | Osborne |
| 6,368,632 B1 | 4/2002 | Mesens et al. |
| 6,379,703 B1 | 4/2002 | Lyons et al. |
| 6,379,704 B2 | 4/2002 | Wright et al. |
| 6,383,471 B1 | 5/2002 | Chen et al. |
| 6,395,293 B2 | 5/2002 | Polson et al. |
| 6,403,114 B1 | 6/2002 | Rickey et al. |
| 6,413,536 B1 | 7/2002 | Gibson et al. |
| 6,431,536 B1 | 7/2002 | Gibson et al. |
| 6,438,961 B2 | 10/2002 | Brodbeck et al. |
| 6,461,631 B1 | 10/2002 | Dunn et al. |
| 6,528,080 B2 | 3/2003 | Dunn et al. |
| 6,534,092 B2 | 3/2003 | Wright et al. |
| 6,565,874 B1 | 5/2003 | Dunn et al. |
| 6,596,316 B2 | 7/2003 | Lyons et al. |
| 6,622,036 B1 | 9/2003 | Suffin |
| 6,630,155 B1 | 10/2003 | Chandrashekar et al. |
| 6,667,061 B2 | 12/2003 | Ramstack et al. |
| 6,673,767 B1 | 1/2004 | Brodbeck et al. |
| 6,750,341 B2 | 6/2004 | Krochmal et al. |
| 6,897,308 B1 | 5/2005 | Venkatasubramanian et al. |
| 6,956,059 B2 | 10/2005 | Coupland |
| 7,041,320 B1 | 5/2006 | Nuwayser |
| RE39,181 E | 7/2006 | Francois et al. |
| 7,118,763 B2 | 10/2006 | Mesens et al. |
| 7,202,360 B2 | 4/2007 | Kim et al. |
| 7,410,635 B2 | 8/2008 | Blondino et al. |
| 7,501,113 B2 | 3/2009 | Blondino et al. |
| 7,691,408 B2 | 4/2010 | Leroux et al. |
| 7,820,202 B2 | 10/2010 | Bodmeier |
| 7,824,700 B2 | 11/2010 | Cleland |
| 7,833,543 B2 | 11/2010 | Gibson et al. |
| 7,927,618 B2 | 4/2011 | Bodmeier |
| 8,114,383 B2 | 2/2012 | Bartholomaus et al. |
| 8,114,429 B2 | 2/2012 | Michal et al. |
| 8,133,507 B2 | 3/2012 | Yum et al. |
| 8,173,148 B2 | 5/2012 | Dadey et al. |
| 8,221,778 B2 | 7/2012 | Siegel et al. |
| 8,236,755 B2 | 8/2012 | Thuresson et al. |
| 8,257,722 B2 | 9/2012 | Michal et al. |
| 8,313,763 B2 | 11/2012 | Margaron et al. |
| 8,324,343 B2 | 12/2012 | Moore et al. |
| 8,329,203 B2 | 12/2012 | Siegel et al. |
| 8,333,989 B2 | 12/2012 | Sukuru |
| 8,377,479 B2 | 2/2013 | Talton |
| 8,415,401 B2 | 4/2013 | Yum et al. |
| 8,486,455 B2 | 7/2013 | Dunn et al. |
| 8,501,216 B2 | 8/2013 | Cleland et al. |
| 8,512,749 B2 | 8/2013 | Sawhney et al. |
| 8,563,023 B2 | 10/2013 | Michal et al. |
| 8,574,552 B2 | 11/2013 | Stroppolo et al. |
| 8,586,103 B2 | 11/2013 | Li et al. |
| 8,741,327 B2 | 6/2014 | Siegel et al. |
| 8,802,127 B2 | 8/2014 | Siegel et al. |
| 8,815,944 B2 | 8/2014 | Leroux et al. |
| 8,852,638 B2 | 10/2014 | Luk et al. |
| 8,877,225 B2 | 11/2014 | Norton et al. |
| 8,877,241 B2 | 11/2014 | Fischer et al. |
| 8,916,202 B2 | 12/2014 | Lebon et al. |
| 9,017,709 B2 | 4/2015 | Griguol et al. |
| 9,044,450 B2 | 6/2015 | Luk et al. |
| 9,168,216 B2 | 10/2015 | Gavin et al. |
| 9,180,197 B2 | 11/2015 | Dadey |
| 9,186,413 B2 | 11/2015 | Dadey |
| 9,221,831 B2 | 12/2015 | Kyle et al. |
| 9,254,268 B2 | 2/2016 | Krayz et al. |
| 9,259,872 B2 | 2/2016 | Hayes et al. |
| 9,308,162 B2 | 4/2016 | Norton |
| 9,326,979 B2 | 5/2016 | Kimura et al. |
| 9,364,518 B2 | 6/2016 | Nadkarni et al. |
| 9,415,034 B2 | 8/2016 | Oliver et al. |
| 9,439,905 B2 | 9/2016 | Siegel et al. |
| 9,468,599 B2 | 10/2016 | Ray, II et al. |
| 9,555,226 B2 | 1/2017 | Zumbrunn et al. |
| 9,597,402 B2 | 3/2017 | Luk et al. |
| 9,717,799 B2 | 8/2017 | Siegel et al. |
| 2002/0064547 A1 | 5/2002 | Chern et al. |
| 2003/0004100 A1 | 1/2003 | Dasch et al. |
| 2003/0009145 A1 | 1/2003 | Struijker-Boudier et al. |
| 2003/0068375 A1 | 4/2003 | Wright et al. |
| 2003/0129219 A1 | 7/2003 | Hong et al. |
| 2004/0018238 A1 | 1/2004 | Shukla |
| 2004/0101557 A1 | 5/2004 | Gibson et al. |
| 2004/0138237 A1 | 7/2004 | Shah |
| 2004/0258731 A1 | 12/2004 | Hayashi et al. |
| 2005/0032781 A1 | 2/2005 | Ehrich |
| 2005/0048123 A1 | 3/2005 | Su et al. |
| 2005/0053647 A1 | 3/2005 | Matusch et al. |
| 2005/0079202 A1 | 4/2005 | Chen et al. |
| 2005/0106214 A1 | 5/2005 | Chen |
| 2005/0112067 A1 | 5/2005 | Kumar et al. |
| 2006/0002979 A1 | 1/2006 | Ashammakhi et al. |
| 2006/0003008 A1 | 1/2006 | Gibson et al. |
| 2007/0077304 A1 | 4/2007 | Luk et al. |
| 2007/0108405 A1 | 5/2007 | Khoo et al. |
| 2007/0196416 A1 | 8/2007 | Chien et al. |
| 2008/0020011 A1 | 1/2008 | Finkelstein et al. |
| 2008/0020039 A1 | 1/2008 | Parikh et al. |
| 2008/0051700 A1 | 2/2008 | Schuster |
| 2008/0287464 A1 | 11/2008 | Wright et al. |
| 2008/0299168 A1 | 12/2008 | Dadey et al. |
| 2009/0048145 A1 | 2/2009 | Hellerbrand et al. |
| 2009/0074708 A1 | 3/2009 | Oliver et al. |
| 2009/0092650 A1 | 4/2009 | Warren et al. |
| 2009/0202481 A1 | 8/2009 | Li et al. |
| 2009/0246265 A1 | 10/2009 | Stinchcomb et al. |
| 2009/0325879 A1 | 12/2009 | Norton |
| 2010/0098735 A1 | 4/2010 | Jain et al. |
| 2010/0173940 A1 | 7/2010 | Leichs et al. |
| 2010/0266655 A1 | 10/2010 | Dadey |
| 2010/0292195 A1 | 11/2010 | Dadey |
| 2010/0330150 A1 | 12/2010 | Venkatesh et al. |
| 2011/0229526 A1 | 9/2011 | Rosenberg et al. |
| 2011/0230816 A1 | 9/2011 | Copp-Howland |
| 2012/0058158 A1 | 3/2012 | Booles |
| 2012/0207843 A1 | 8/2012 | Lebon et al. |
| 2013/0023553 A1 | 1/2013 | Jude-Fishburn et al. |
| 2013/0129828 A1 | 5/2013 | Talton |
| 2013/0143909 A1 | 6/2013 | Chong et al. |
| 2013/0171202 A1 | 7/2013 | Gutierro et al. |
| 2013/0177603 A1 | 7/2013 | Gutierro Aduriz et al. |
| 2013/0210751 A1 | 8/2013 | Dong et al. |
| 2013/0231359 A1 | 9/2013 | Chong et al. |
| 2013/0289053 A1 | 10/2013 | Wright et al. |
| 2013/0331803 A1 | 12/2013 | Fleschhut et al. |
| 2014/0023692 A1 | 1/2014 | Du Toit et al. |
| 2014/0134261 A1 | 5/2014 | Singh et al. |
| 2014/0271869 A1 | 9/2014 | Richey et al. |
| 2014/0308352 A1 | 10/2014 | Wright et al. |
| 2014/0363487 A1 | 12/2014 | Hille et al. |
| 2015/0005323 A1 | 1/2015 | Dadey et al. |
| 2015/0099767 A1 | 4/2015 | Dadey et al. |
| 2015/0209555 A1 | 7/2015 | Ruane et al. |
| 2015/0231258 A1 | 8/2015 | Luk et al. |
| 2015/0250738 A1 | 9/2015 | Yum et al. |
| 2015/0359891 A1 | 12/2015 | Chen et al. |
| 2016/0106847 A1 | 4/2016 | Dadey et al. |
| 2016/0303038 A1 | 10/2016 | Yadav et al. |

FOREIGN PATENT DOCUMENTS

| | | |
|---|---|---|
| EP | 0 532 546 A1 | 3/1993 |
| EP | 0 532 546 B1 | 3/1993 |

(56) References Cited

FOREIGN PATENT DOCUMENTS

| | | |
|---|---|---|
| EP | 0 537 559 A1 | 4/1993 |
| EP | 0 537 559 B1 | 4/1993 |
| EP | 0 572 494 A1 | 12/1993 |
| EP | 0 572 494 B1 | 12/1993 |
| EP | 0 730 865 A1 | 9/1996 |
| EP | 0 730 865 B1 | 9/1996 |
| EP | 0998917 | 5/2000 |
| EP | 1 006 935 A1 | 6/2000 |
| EP | 1 006 935 B1 | 6/2000 |
| EP | 1 015 032 A2 | 7/2000 |
| EP | 1 181 935 A2 | 2/2002 |
| EP | 1 181 935 A3 | 2/2002 |
| EP | 1 181 935 B1 | 2/2002 |
| EP | 1210942 | 6/2002 |
| EP | 1 644 002 A1 | 4/2006 |
| EP | 1 644 002 B1 | 4/2006 |
| EP | 1649850 | 4/2006 |
| EP | 1317254 | 2/2007 |
| EP | 1248596 | 3/2007 |
| EP | 1 830 900 A1 | 9/2007 |
| EP | 1 940 351 A2 | 7/2008 |
| EP | 1 940 351 B1 | 7/2008 |
| EP | 2 081 574 A1 | 7/2009 |
| EP | 2 361 609 A1 | 8/2011 |
| EP | 2 361 609 B1 | 8/2011 |
| EP | 2 445 487 A2 | 5/2012 |
| EP | 2529756 | 12/2012 |
| EP | 2361609 | 7/2013 |
| EP | 2 797 602 A2 | 11/2014 |
| EP | 2 152 315 B1 | 1/2016 |
| GB | 806876 A | 1/1959 |
| GB | 873526 A | 7/1961 |
| GB | 887872 A | 1/1962 |
| GB | 2165148 | 4/1986 |
| IN | 1535/DEL/2004 | 8/2006 |
| JP | S61-37725 | 2/1986 |
| JP | H04-056736 | 5/1992 |
| JP | H05-078634 | 3/1993 |
| JP | 5286850 B2 | 11/1993 |
| JP | 9511741 A | 11/1997 |
| JP | H09-315957 | 12/1997 |
| JP | 2001-509146 | 7/2001 |
| JP | 2001-516728 | 10/2001 |
| JP | 2002-528403 A | 9/2002 |
| JP | 2002-537221 A | 11/2002 |
| JP | 2003-063954 | 3/2003 |
| JP | 2004-511431 | 4/2004 |
| JP | 2004-510807 A | 4/2008 |
| JP | 2009-510116 A | 3/2009 |
| JP | 2010-506965 A | 3/2010 |
| JP | 2010-519218 A | 6/2010 |
| JP | 2003-514006 A | 4/2013 |
| WO | WO-93/23019 A1 | 11/1993 |
| WO | WO-95/27481 A1 | 10/1995 |
| WO | WO-96/21427 A1 | 7/1996 |
| WO | WO-96/39095 A1 | 12/1996 |
| WO | 1998/27963 | 6/1998 |
| WO | WO-98/58685 A1 | 12/1998 |
| WO | 99/13913 | 5/1999 |
| WO | WO-00/06117 A1 | 2/2000 |
| WO | 00/24374 | 5/2000 |
| WO | WO-01/35929 A2 | 5/2001 |
| WO | WO-01/35929 A3 | 5/2001 |
| WO | 02/08351 | 1/2002 |
| WO | 2002/00137 | 1/2002 |
| WO | WO-02/30393 A2 | 4/2002 |
| WO | WO-02/30393 A3 | 4/2002 |
| WO | WO-02/038185 A2 | 5/2002 |
| WO | WO-02/038185 A3 | 5/2002 |
| WO | 2002/067895 | 9/2002 |
| WO | 2002/076344 | 10/2002 |
| WO | 2003/041684 | 5/2003 |
| WO | 2003/041685 | 5/2003 |
| WO | 2003/041757 | 5/2003 |
| WO | 2004/000269 | 12/2003 |
| WO | WO-2004/020439 A2 | 3/2004 |
| WO | WO-2004/020439 A3 | 3/2004 |
| WO | 2004/032980 | 4/2004 |
| WO | 2004/043432 | 5/2004 |
| WO | WO-2004/037259 A1 | 5/2004 |
| WO | 2004/026357 | 9/2004 |
| WO | 2004/094414 | 11/2004 |
| WO | 2005/048989 | 6/2005 |
| WO | 2005/070332 | 8/2005 |
| WO | 2005/089670 | 9/2005 |
| WO | 2005/115346 | 12/2005 |
| WO | WO-2006/041942 A2 | 4/2006 |
| WO | WO-2006/041942 A3 | 4/2006 |
| WO | WO-2006/063794 A1 | 6/2006 |
| WO | 2007/084460 | 1/2007 |
| WO | WO-2007/011955 A2 | 1/2007 |
| WO | WO-2007/011955 A3 | 1/2007 |
| WO | WO-2007/041410 A2 | 4/2007 |
| WO | WO-2007/041410 A3 | 4/2007 |
| WO | WO-2008/045516 A1 | 4/2008 |
| WO | WO-2008/100532 A1 | 8/2008 |
| WO | WO-2008/153611 A2 | 12/2008 |
| WO | WO-2008/153611 A3 | 12/2008 |
| WO | 2009/100222 | 2/2009 |
| WO | 2011/151355 | 12/2011 |
| WO | 2011/151356 | 12/2011 |
| WO | 2012/074883 | 6/2012 |
| WO | WO-2014/081343 A2 | 5/2014 |
| WO | WO-2014/081343 A3 | 5/2014 |
| WO | 2014/164754 | 10/2014 |

OTHER PUBLICATIONS

Huang, et al., "Pharmacokinetics of the novel antipsychotic agent risperidone and the prolactin response in healthy subjects," *Clinical Pharmacology & Therapeutics*, 54(3), pp. 257-268. Sep. 1993.
Opponent's Grounds of Appeal in patent No. EP2361609 dated Mar. 29, 2016, pp. 1-13.
Opponent's Further Submission in EP Patent No. 2361609, dated Mar. 6, 2017, pp. 1-14.
Patentee's Response to Grounds of Appeal in EP Patent No. 2361609, dated Aug. 12, 2016, pp. 1-53.
Sigma-Aldrich website "Amitriptyline hydrochloride" pp. 1-4.
Wang, et al., "Structure formation in injectable poly(lactide-co-glycolide) depots," *J. Control. Rel.*, 90, pp. 345-354, 2003.
Wang, et al., "Drug release from injectable depots: two different in vitro mechanisms", *J. of Controlled Rel.*, 99, pp. 207-216, 2004.
Wright, Jeremy, "Experimental Report—In Vitro Release Profiles for Formulations containing Amitriptyline hydrochloride," submitted in European Patent No. 2,361,609, Aug. 10, 2016.
U.S. Appl. No. 14/658,072, filed Mar. 13, 2015, Yum, et al.
Berge, L., et al., "Pharmaceutical Salts", *J. of Pharmaceut. Sci.*, vol. 66:1, Jan. 1977, pp. 1-19.
Carraway KM, Meador SK, Sullivan SA, Gibson JW, Tipton AJ, Drug release from a controlled release aerosol: Effects of formulation variables Southern Biosystems, Inc., Birmingham, ALAAPS Indianapolis Nov. 2000.
Communication of a Notice of Opposition, Notice of Opposition and Opponents Grounds of Opposition, from EP 2361609, mailed May 7, 2014.
Desai, et al., "Surface modification of polymer biomaterials for reduced thrombogenicity", *Polym. Mater. Sci. Eng.* 63:731-735, 1990.
Dong, et al., "Development of injectable biodegradable in-situ forming gel implants", *Progress in Pharmaceutical Sciences*, 31:109-113, 2007.
Eliaz, et al., "Characterization of a polymeric PLGA-injectable implant delivery system for the controlled release of proteins", *J. Biomed. Mater. Res.* 2000, 50:388-396.
Erickson NM, Kines PP, Meador SK, Middleton JC, Williams CT, Williams JC, "An in vitro degradation study comparing poly(DL-lactide co-glycolide) with acid end groups and ester end groups", 20th Southern Biomedical Engineering Conference 2001.

(56) References Cited

OTHER PUBLICATIONS

English language translation of Office Action dated May 15, 2012, from Japanese Application No. 2008-533726, which is a family member of the present application.

English language translation of Japanese Office Action dated Apr. 14, 2015 for JP2013-002422.

Gomeni, R., et al., "A model-based approach to characterize the population pharmacokinetics and the relationship between the pharmacokinetic and safety profiles of RBP-7000, a new, long-acting, sustained-release formulation of Risperidone", *J. Clin. Pharmaco.* 58(10) 1010-1019 2013.

Hatefi, et al., "Biodegradable injectable in situ forming drug delivery system", *J. of Contr. Rel.* vol. 80, Jan. 1, 2002, pp. 9-28.

Hou H, etal., *China Med. Press* pp. 223-226, 2011.

Johnson CA, Thompson DL, Jr., Sullivan SA, Gibson JW, Tipton AJ, Simon BW, Burns PJ, "Biodegradable delivery systems for Estradiol: Comparison between Poly (DL-lactide) microspheres and the SABER delivery system", *Proceed Int'l. Symp. Control. Rel. Bioact. Mater.*, 26 (1999), Controlled Release Society, Inc.

Kulkarni RK, et al., "Polylactic acid for surgical implants", *Arch. Surg.* vol. 93, Nov. 1966, 839-843.

Laffont, C., et al., "Population pharmacokinetic modeling and simulation to guide dose selection for RBP-7000, a new sustained-release formulation for Risperidone", *Clin. Pharma.* 55(1) 93-103, 2014.

Laffont, C., et al., "Population pharmacokinetics and prediction of dopamine D2 receptor occupancy after multiple doses of RBP-7000, a new sustained-release formulation of risperidone, in schizophrenia patients on stable oral risperidone treatment", *Clin. Pharmacokinetics*, 53:533-543, 2014.

Lambert et al., Journal of Controlled Release, 1995 33:189-195.

Lin, et al., Á novel risperidone-loaded SAIB-PLGA mixture matrix depot with a reduced burst release: effect of solvents and PLGA on drug release behaviors in vitro/in vivo, *J. Mater. Sci.: Mater. Med.* (2012) 23:443-455.

Lu, et al., "Sucrose Acetate Isobutyrate as an in situ forming system for sustained riperidone release", *J. Pharm. Sci.*, vol. 96, No. 12, Dec. 2007, 3252-3262.

Lu, et al., "In vivo evaluation of risperidone-SAIB in situ system as a sustained release delivery system in rats", *Eur. J. Pharma and Biopharm.*, 68 (2008) 422-429.

Middleton, et al., Medical device and diagnostic industry news products and suppliers 1998.

Middleton JC, Yarbrough JC, "The effect of PEG end groups on the degradation of a 75/25 poly(DL-lactide-co-glycolide", *Society for Biomaterials* 1999.

Okumu FW, Daugherty A, Dao LN, Fielder PJ, Brooks D, Sane S, Sullivan SA, Tipton AJ, Cleland JL, "Evaluation of the SABER TM delivery system for sustained release of growth hormone formulation design and in vivo assessment" 2001.

Okumu FW, Daugherty A, Sullivan SA, Tipton AJ, Cleland JL, "Evaluation of SABER TM as a local delivery system for rhVEGF-formulation design and in vitro assessment", 2000.

Okumu FW, Dao Le, Fielder PJ, Dybdal N, Brooks D, Sane S, Cleland JL, "Sustained delivery of human growth hormone from a novel gel system: SABER TM", *Biomaterials* 23 (2002) 4353-4358.

Opponent written submissions in patent No. EP2361609 dated Sep. 10, 2015 pp. 1-6.

Opposition Minutes and Opinion in patent No. EP2361609 dated Nov. 27, 2015 pp. 1-20.

Patent Owner's written submissions in patent No. EP2361609 dated Sep. 10, 2015 pp. 1-9.

Patent owners Experimental report in patent No. EP2361609 dated Aug. 18, 2015.

Summons to Oral Proceedings from European Patent Office in Opposition against EP Patent No. 2361609 dated Feb. 16, 2015. pp. 1-6.

Patent owner's written submission in opposition against EP2361609 dated Nov. 19, 2014 pp. 1-10.

Penco M, et al., "A new chain extension reaction on poly(lactic-glycolic acid) (PLGA) thermal oligomers leading to high molecular weight PLGA-based polymeric products," *Polymer International*, 46:203-216, 1998.

Ravivarapu, et al., Journal of Pharmaceutical Sciences 89:732-741.

"Relday: First once-monthly subcutaneous risperidone for the management of schizophrenia," partnering overview, 2013.

Shakeel, F., et al., "Solubility of antipsychotic drug risperidone in Transcutol + water co-solvent miztures at 298.15 to 333.15 K" *J. of Molec. Liq.* 191(2014) 68-72.

Sinha & Trehan, "Biodegradable Microspheres for Parenteral Delivery", *Critical Reviews in Therapeutic Drug Carrier Systems*, 22(6): 535-602 (2005).

Smith DA, Tipton AJ, "A novel parenteral delivery system", AAPS—Presentation TDD 7270 Annual Meeting, Seattle, WA (1996).

Sullivan SA, Yarbrough JC, Fengl RW, Tipton AJ, Gibson JW, "Sustained release of orally administered active using SABER TM delivery system incorporated into soft gelatin capsules", *Proceed. Int'l. Symo. Control. Rel. Bioact. Mater.*, 25 (1998), Controlled Release Society, Inc.

Sullivan SA, Meador SK, Carraway KM, Williams JC, Gibson JW, Tipton AJ, "Sustained release of lysozyme from the SABER delivery system", AAPS New Orleans, LA 1999.

Sullivan SA, Meador SK, Dodson KM, Williams JC, Gibson JW, Tipton AJ, "Sustained release of lysozyme from the SABER delivery system", Poster, Southern Biosystems, Inc. Birmingham AL AAPS New Orleans, LA 1999.

Sullivan SA, Meador SK, Dodson KM, Tipton AJ, Gibson JW, "Incorporation of polymer microparticles into sucrose acetate isobutyrate reduces burst and extends release", *Proceed. Int'l. Symp. Control. Rel. Bioact. Mater.*, 27, Controlled Release Society, Inc. (2000).

Tipton AJ, "Sucrose Acetate Isobutyrate (SAIB) for Parenteral Delivery", Reprinted from Modified-Release Drug Delivery Technology, Rathbone, Hadgraft, Roberts (Eds.), 2002 Marcel Dekker, Inc.

Wang, et al., "Synthesis, characterization, biodegration, and drug delivery application of biodegradable Iactic/glycolic acid polymers: I. Synthesis and characterization," *J. Biomater. Sci Polymer Edn*, vol. 11, No. 3, pp. 301-318 (2000).

Written Opinion of the International Searching Authority for International Application No. PCT/US2014/023397 dated Sep. 15, 2015.

Yapar, E., et al., "Injectable In Situ forming microparticles: A novel drug delivery system", *Tropical J. of Pharmaceut. Res.*, 11(2) 307-318, Apr. 2012.

http://www.absorbables.com/technical/inherent_viscosity.html, published online 2013.

"U.S. Appl. No. 14/490,082, Non Final Office Action dated Oct. 10, 2014", 12 pgs.

"U.S. Appl. No. MX/a/2009/012781, Voluntary Amendment filed", 11 pgs.

"Australian Application Serial No. 2008262545, Examiner Report dated Jun. 19, 2013", 5 pgs.

"Australian Application Serial No. 2008262545, Examiner Report dated Oct. 15, 2012", 5 pgs.

"Australian Application Serial No. 2008262545, Response filed May 27, 2013 to Examiner Report dated Oct. 15, 2012", 26 pgs.

"Australian Application Serial No. 2008262545, Response filed Nov. 13, 2013 to Examiner Report dated Jun. 19, 2013", 21 pgs.

"Canadian Application Serial No. 2,687,979, Office Action dated May 7, 2014", 4 pgs.

"Chinese Application Serial No. 200880100394.0, Decision on Rejection dated Sep. 3, 2013", (w/ English Translation), 11 pgs.

"Chinese Application Serial No. 200880100394.0, Office Action dated Apr. 2, 2013", 10 pgs.

"Chinese Application Serial No. 200880100394.0, Office Action dated Jul. 25, 2012", 25 pgs.

"Chinese Application Serial No. 200880100394.0, Request for Reexamination filed Dec. 18, 2013 in response to Decision on Rejection dated Sep. 3, 2013", (w/ English Translation), 11 pgs.

"Chinese Application Serial No. 200880100394.0, Response filed Mar. 9, 2012 to Office Action dated Oct. 25, 2011", 16 pgs.

(56) References Cited

OTHER PUBLICATIONS

"Chinese Application Serial No. 200880100394.0, Response filed Jun. 17, 2013 to Office Action dated Apr. 2, 2013", (w/ English Translation of Amended Claims), 19 pgs.
"Chinese Application Serial No. 200880100394.0, Response filed Oct. 9, 2012 to Office Action dated Jul. 25, 2012", CN Response Only, 12 pgs.
"European Application Serial No. 08725543.6, Office Action dated Feb. 6, 2013", 10 pgs.
"European Application Serial No. 08725543.6, Response filed Jan. 17, 2011 to Noting Loss of Rights dated Nov. 17, 2010 and Office Action dated Mar. 31, 2010", 16 pgs.
"European Application Serial No. 08725543.6, Response filed Jul. 11, 2013 to Office Action dated Feb. 6, 2013", 20 pgs.
"European Application Serial No. 08725543.6, Summons to Attend Oral Proceedings dated Jun. 12, 2014", 7 pgs.
European Application Serial No. 08725543.6, Communication Noting Loss of Rights pursuant to Rule 112(1) CPC dated Nov. 17, 2010, 2 pgs.
European Application Serial No. 08725543.6, Office Action dated Mar. 31, 2010, 5 pgs.
European Patent Office, Preliminary Opinion by the Opposition Division on the Opposition to European Patent No. 2 152 315 (dated Sep. 8, 2017) (18 pages).
"Form 10-K QLT Inc.", <URL:http://www.oltinc.com/OLTincidownloads/investment110k-2006.pdf>, (2006), 137 pgs.
"Gel: From Wikipedia, the free encyclopedia", [online]. [retrieved on Jul. 23, 2013]. Retrieved from the Internet: <URL: http://en.wikipedia.org/wiki/Gel>, (2013), 5 pgs.
International Application Serial No. PCT/US2008/001928, International Search Report dated Jun. 10, 2009, 3 pages.
International Application Serial No. PCT/US2008/001928, Written Opinion dated Jun. 10, 2009, 8 pages.
"International Application Serial No. PCT/US2008/001928, International Preliminary Report on Patentability dated Dec. 10, 2009", 9 pgs.
"Japanese Application Serial No. 2010-509326, Office Action dated Jan. 22, 2013", 10 pgs.
"Japanese Application Serial No. 2010-509326, Office Action dated May 14, 2013", (w/ English Translation), 4 pgs.
"Japanese Application Serial No. 2010-509326, Response filed Apr. 18, 2013 to Office Action dated Jan. 22, 2013", 21 pgs.
"Mexican Application Serial No. MX/a/2009/012781, Office Action dated Jun. 24, 2013". (w/ English Summary), 7 pgs.
"Mexican Application Serial No. MX/a/2009/012781, Office Action dated Mar. 5, 2014", 4 pgs.
"Mexican Application Serial No. MX/a/2009/012781, Office Action dated Nov. 21, 2012".
"Mexican Application Serial No. MX/a/2009/012781, Response filed Feb. 28, 2013 to Office Action dated Nov. 21, 2012", 15 pgs.
"Mexican Application Serial No. MX/a/2009/012781, Response filed Nov. 4, 2013 to Office Action dated Jun. 24, 2013", 17 pgs.
"New Zealand Application Serial No. 581862, Office Action dated Feb. 9, 2012", 2 pgs.
"New Zealand Application Serial No. 581862, Response filed Jan. 18, 2012 to Office Action dated Oct. 19, 2010", 30 pgs.
"New Zealand Application Serial No. 581862, Response filed May 10, 2012 to Office Action dated Feb. 9, 2012", 12 pgs.
New Zealand Application Serial No. 581862, First Examiner Report dated Oct. 19, 2010, 3 pages.
"New Zealand Application Serial No. 597621, Examiner Report dated May 16, 2013", 2 pgs.
"New Zealand Application Serial No. 597621, Examiner Report dated Jan. 20, 2012", 3 pgs.
"New Zealand Application Serial No. 597621, Response filed Apr. 30, 2013 to Examiner Report dated Jan. 20, 2012", 11 pgs.
"New Zealand Application Serial No. 597621, Response filed Jun. 7, 2013 to Examiner Report dated May 16, 2013", 7 pgs.
"New Zealand Application Serial No. 611649, First Examination Report dated Jun. 11, 2013", 3 pgs.

New Zealand Application Serial No. 611649, Response filed Jan. 16, 2014 to First Examination report dated Jun. 11, 2013, 4 pages.
"New Zealand Application Serial No. 611649, Response filed Mar. 21, 2014 to Subsequent Examiners Report dated Feb. 5, 2014", 2 pgs.
"New Zealand Application Serial No. 611649, Subsequent Examiners Report dated Feb. 5, 2014", 2 pgs.
"New Zealand Application Serial No. 611649, Third Examination Report dated Apr. 7, 2014", 1 pg.
Ahmed, T.A. et al. (Jun. 2015, e-published Mar. 20, 2014). "Biodegradable injectable in situ implants and microparticles for sustained release of montelukast: in vitro release, pharmacokinetics, and stability," AAPS PharmSciTech 15(3):772-780.
Ahmed, T.A. et al. (Oct. 2012, e-published Jun. 29, 2012). "Development of biodegradable in situ implant and microparticle injectable formulations for sustained delivery of haloperidol," J Pharm Sci 101(10):3753-3762.
Aird, J. (Apr. 2003). Controlled Release—SMi Conference. Feb. 12-13, 2003, London,UK, IDrugs 6(4):334-336.
Anonymous, "Form 10-K QLT Inc.", Internet Article, [online]. [retrieved May 14, 2009]. Retrieved from the Internet: <URL: http://www.gltinc.corn/QLTincl_downloadslinvestment/ 10K-2006.pdf>, (Mar. 1 2007), 71 pgs.
Anonymous, "U.S. Securities and Exchange Commission", QLT Inc., 10-K Title Page, [online]. [retrieved May 14, 2009]. Retrieved from the Internet: <URL: http://www.sec.gov/Archivesledgaridatal827809/000094523407000108/0000945234-07-000108-ndex.idea.htm>, (Mar. 1 2007), 1 pg.
Astaneh, R. et al. (Jan. 2009). "Changes in morphology of in situ forming PLGA implant prepared by different polymer molecular weight and its effect on release behavior," J Pharm Sci 98(1):134-145.
Babu, R.J. et al. (May-Jun. 2005). "Effect of penetration enhancers on the transdermal delivery of bupranolol through rat skin," Drug Deliv 12(3):165-169.
Baker, D.L. et al. (Oct. 2004). "Gonadotropin-releasing hormone agonist: a new approach to reversible contraception in female deer," J Wildl Dis 40(4):713-724.
Bartsch, W. et al. (1976). "Acute Toxicity in Various Solvents in the Mouse and Rat," Arzneim-Forsch, Drug Res 26:1581-1583.
Basu, S.K. et al. (Mar. 2004). "Protein crystals for the delivery of biopharmaceuticals," Expert Opin Biol Ther 4(3):301-317.
Becci, P.J. et al. (1983). "Subchronic feeding study in beagle dogs of N-methylpyrrolidone," J Appl Toxicol 3(2):83-86.
Berges, R. et al. (2005). "Eligard®: Pharmacokinetics, effect on Testosterone and PSA Levels and Tolerability," European Urology Supplements 4:20-25.
Boongird, A. et al. (Jan. 2011). "Biocompatibility study of glycofurol in rat brains," Exp Biol Med 236(1):77-83.
Bowersock, T.L. et al. (1999). "Vaccine delivery to animals," Adv Drug Deliv Rev 38(2):167-194.
Bromberg, L.E. et al. (Jul. 31, 2000). "Sustained release of silver from periodontal wafers for treatment of periodontitis," J Control Release 68(1):63-72.
Buggins, T.R. et al. (Dec. 22, 2007). "The effects of pharmaceutical excipients on drug disposition," Adv Drug Deliv Rev 59(15):1482-1503.
Chandrashekar, B.L. et al. (Jul. 1999). "Sustained Release of Leuprolide Acetate from an In-situ Forming Biodegradable Polymeric Implant as the Delivery Vehicle," Proceed Int'l Symp Control Rel Bioact Mater 26, 3 pages.
Chen, F.A. et al. (Jul. 2003). "Biodegradable polymer-mediated intratumoral delivery of cisplatin for treatment of human head and neck squamous cell carcinoma in a chimeric mouse model," Head Neck 25(7):554-560.
Cheng, Y. et al. (Dec. 2013, e-published Oct. 1, 2013). "Thermosensitive hydrogels based on polypeptides for localized and sustained delivery of anticancer drugs," Biomaterials 34(38):10338-10347.
Chu, F.M. et al. (Sep. 2002). "A clinical study of 22.5 mg. La-2550: A new subcutaneous depot delivery system for leuprolide acetate for the treatment of prostate cancer," Journal of Urology 168(3):1199-1203.

(56) References Cited

OTHER PUBLICATIONS

Coonts, B.A. et al. (Oct. 1993). "Plasma Concentrations of Naltrexone Base Following Subcutaneous and Intramuscluar Injections of Atrigel™ Formulations in Dogs," Pharmaceutical Research: Official Journal of the American Association of Pharmaceutical Scientists PHREEB 10(10):PDD 7071, 2 pages.

Cox, M.C. et al. (Aug. 2005). "Leuprolide acetate given by a subcutaneous extended-release injection: less of a pain?" Expert Rev Anticancer Ther 5(4):605-611.

Crawford, E.D. et al. (Feb. 2006). "A 12-month clinical study of LA-2585 (45.0 mg): a new 6-month subcutaneous delivery system for leuprolide acetate for the treatment of prostate cancer," Journal of Urology 175(2):533-536.

Dadey, E.J. (2008). The Atrigel Drug Delivery System. In: Rathbone et al Eds, Modified-Release Drug Delivery Technology, 2nd Ed., New York, pp. 183-190.

Dernell, W.S. et al. (1998). "Apparent interaction of dimethyl sulfoxide with cisplatin released from polymer delivery devices injected subcutaneously in dogs," J Drug Target 5(5):391-396.

Dewan, I. et al. (2011). "Study of Release Kinetics of Dexamethasone from Biodegradable PLA In-Situ Implants," International Journal of Pharmaceutical Science and Research 2(11): 3039-3045.

Domb, A.J. et al. (1989). "Solid-State and Solution Stability of Poly(anhydrides) and Poly(esters)," Macromolecules 22(5):2117-2122.

Dunn, R.L. et al (1996). "Sustained Release of Cisplatin in Dogs from an Injectable Implant Delivery System," Journal of Bioactive and Compatible Polymers, 11:286-300.

Dunn, R.S., (2003). "The Atrigel Drug Delivery System," Modified-Release Drug Delivery Technology, Edited by Rathbone, Hadgraft, Roberts, Marcel Dekker, Inc., Chapter 54, pp. 647-655.

Duysen, E.G. et al (1992). "Bioactivity of Polypeptide Growth Factors Released from the Atrigel Drug Delivery System," PHREEB, 9(10):S73, Abstract No. 2028.

Duysen, E.G. et al (1993). "Release of Bioactive Growth Factors from the ATRIGEL Delivery System in Tibial Defect and Dermal Wound Models," PHREEB, 10(10):S83, Abstract No. 2043.

Duysen, E.G. et al (1994). "An Injectable, Biodegradable Delivery System for Antineoplastic Agents," PHREEB, 11(10):S88, Abstract No. 2071.

Eliaz, R.E. et al. (Dec. 2000). "Delivery of soluble tumor necrosis factor receptor from in-situ forming PLGA implants: in-vivo," Pharm Research 17(12):1546-1550.

Evans, H.C., et al (2004). "Leuprorelin: Subcutaneous Depot Formulation (ELIGARD) for Advanced Prostate Cancer," Am J. Cancer, 3(3):197-201.

FDA Document K982865 (1998). Atrix Laboratories, Inc. 13 pages.
FDA Document K994137 (2000). Atrix Laboratories, Inc. 9 pages.
Fleischhacker et al. "Treatment of schizophrenia with long acting injectable risperidone: a 12-month open-label trial of the first acting second-generation antipsychotic" in the J. Clin. Psychiatry: Oct. 2003;64(10)1250-7.

Frank, K.R. et al (1994). "Controlled Release of Bioactive Growth Factors from a Biodegradable Delivery System," PHREEB, 11(10):S88, Abstract No. 2070.

Furuishi, T. et al. (Jul. 2007). "Effect of permeation enhancers on the in vitro percutaneous absorption of pentazocine," Biol Pharm Bull 30(7):1350-1353.

Gerentes, P. et al. (2002). "Study of a chitin-based gel as injectable material in periodontal surgery," Biomaterials 23(5):1295-1302.

Gou, M. et al. (Apr. 2010). "Polymeric matrix for drug delivery: honokiol-loaded PCL-PEG-PCL nanoparticles in PEG-PCL-PEG thermosensitive hydrogel," J Biomed Mater Res A 93(1):219-226.

Griffeth, R.J. et al. (2002). "Is Lucteal Production of PGF2α Required for Luteolysis?" Biology of Reproduction 66(Supplement 1), Abstract 465, 2 pages.

Hempel, G. et al. (May 1, 2007). "Cytotoxicity of dimethylacetamide and pharmacokinetics in children receiving intravenous busulfan," J Clin Oncol 25(13):1772-1778.

Ibrahim, H.M. et al. (Jan. 2014, e-published Jan. 9, 2013). "Development of meloxicam in situ implant formulation by quality by design principle," Drug Dev Ind Pharm 40(1):66-73.

Jain, R.A. (Dec. 2000). "The manufacturing techniques of various drug loaded biodegradable poly(lactide-co-glycolide) (PLGA) devices," Biomaterials 21(23):2475-2490.

Jaiswal, J. et al. (Mar. 1, 1999). "Transdermal delivery of naloxone: ex vivo permeation studies," Int J Pharm 179(1):129-134.

Jarr, E.M. et al. (Jul. 1999). "Sustained Release of Lidocaine from an Injectable Implant System for Treatmenr of Post-Operative," Proceedings Int'l Symp Control Rel Bioact Materials Abstract #5427, 4 pages.

Johnson, O.L. et al. (Jun. 1997). "The stabilization and encapsulation of human growth hormone into biodegradable microspheres," Pharm res 14(6):730-735.

Kan, P. et al. (Jul. 21, 2005). "Thermogelling Emulsions for Vascular Embolization and Sustained Release Drugs," Journal of Biomedical Materials Research 75B(1):185-192.

Karatas, A. et al. (2006). "Studies of Release of Ketorolac Tromethamin and Indomethacin from Opthalmic Hydrogel Inserts," Ankara Ecz Fak Derg 35(4)255-268.

Kaul, S. et al. (Feb. 2000). "Polymeric-based perivascular delivery of a nitric oxide donor inhibits intimal thickening after balloon denudation arterial injury: role of nuclear factor-kappaB," J Am Coll Cardiol 35(2):493-501.

Kelava, T. et al. (2011). "Biological Actions of Drug Solvents," Periodicum Biologorum 113(3):311-320.

Kissel, T. (Jan. 2002). "ABA-triblock copolymers from biodegradable polyester A-blocks and hydrophilic poly(ethylene oxide) B-blocks as a candidate for in situ forming hydrogel delivery systems for proteins," Adv Drug Deliv Rev 54(1):99-134.

Kranz, H. et al. (Jan. 5, 2001). "Myotoxicity studies of injectable biodegradable in-situ forming drug delivery systems," Int J Pharm 212(1):11-18.

Lee, K.P. et al. (Aug. 1987). "Toxicity of N-methyl-2-pyrrolidone (NMP): teratogenic, subchronic, and two-year inhalation studies," Fundam Appl Toxicol 9(2):222-235.

Li, M. et al. (Nov. 2003). "A novel, non-prostanoid EP2 receptor-selective prostaglandin E2 agonist stimulates local bone formation and enhances fracture healing," Bone Miner Res 18(11):2033-2042.

Lynch, G.S. et al. (Nov. 2004). "Emerging drugs for sarcopenia: age-related muscle wasting," Expert Opin Emerg Drugs 9(2):345-361.

Madhu, M. et al. (Nov.-Dec. 2009). "Biodegradeable Injectable Implant Systems for Sustained DeliveryUsing Poly (Lactide-Co-Glycolide) Copolymers," International Journal of Pharmacy and Pharmaceutical Sciences Vol. 1, Suppl 1, 103-107.

Makadia, H.K. et al. (Sep. 1, 2011, e-published Aug. 26, 2011). "Poly Lactic-co-Glycolic Acid (PLGA) as Biodegradable Controlled Drug Delivery Carrier," Polymers 3(3):1377-1397.

Malik, K. et al. (2010). "Atrigel: A potential parenteral controlled drug delivery system," Der Pharmacia Sinica 1(1):74-81.

Matschke, C. et al. (Dec. 2002). "Sustained-release injectables formed in situ and their potential use for veterinary products," J Control Release 85(1-3):1-15.

McLeod, D.G. et al. (Feb. 2003). "Hormonal therapy: historical perspective to future directions," Urology 61(Suppl 2A):3-7.

Mealy (2004). "Treatment of Metabolic Disorders by Condition," Annual Update 2003/2004-Drugs of the Future 29(8):843-872.

Medlicott, N.J. et al. (Jun. 23, 2004). "Sustained release veterinary parenteral products," Adv Drug Deliv Rev 56(10):1345-1365.

Mendelson, J.E. et al (Apr. 2011, e-published Dec. 8, 2010). "Lack of effect of sublingual salvinorin A, a naturally occurring kappa opioid, in humans: a placebo-controlled trial," Psychopharmacology 214(4):933-939.

Miller, R.A. et al. (Sep. 1977). "Degradation rates of oral resorbable implants (polylactates and polyglycolates): rate modification with changes in PLA/PGA copolymer ratios," Biomed Mater Res 11(5):711-719.

Mottu, F. et al. (Apr. 2000). "In vitro assessment of new embolic liquids prepared from preformed polymers and water-miscible solvents for aneurysm treatment," Biomaterials 21(8):803-811.

(56) References Cited

OTHER PUBLICATIONS

Mownika, G. et al. (2012). "Formulation and Evaluation of Simvastatin Injectable in situ Implants," American Journal of Drug Discovery and Development 2(2):87-100.

Nahata, T. et al. (Mar.-Apr. 2009). "Formulation optimization of long-acting depot injection of aripiprazole by using D-optimal mixture design," PDA J Pharm Sci Technol 63(2):113-122.

Notice of Opposition dated Oct. 20, 2016, for EP Application No. EP 08725543.6, 5 pages.

Nyberg, S. et al. (Jun. 1999). "Suggested minimal effective dose of risperidone based on PET-measured D2 and 5-HT2A receptor occupancy in schizophrenic patients," Am J Psychiatry 156(6):869-875.

Olby, N. (Sep. 2010). "The pathogenesis and treatment of acute spinal cord injuries in dogs," Vet Clin North Am Small Anim Pract 40(5):791-807.

Omidfar, K. et al. (2002). "Stabilization of Penicillinase-Hapten Conjugate for Enzyme Immunoassay," Journal of Immunoassay & Immunochemistry 23(3):385-398.

Opposition to European Patent No. 2152315 dated Oct. 6, 2016, 12 pages.

Packhaeuser, C. B, et al., "In situ forming parenteral drug delivery systems: an overview", Eur J Pharm Biopharm., 58(2), (Sep. 2004), 445-55.

Panaccione, C. et al. (1997). "Use of a Trinomial Distribution Probability Model in Development of a Tier-Testing Scheme for Content Uniformity Testing," Drug Information Journal 31:903-909.

Paralkar, V.M. et al. (May 27, 2003, e-published May 14, 2003). "An EP2 receptor-selective prostaglandin E2 agonist induces bone healing," PNAS USA 100(11):6736-6740.

Parent, M. et al. (Nov. 28, 2013, e-published Sep. 1, 2013). "PLGA in situ implants formed by phase inversion: critical physicochemical parameters to modulate drug release," J Control Release 172(1):292-304.

Patel, R.B. et al. (Nov. 1, 2010, e-published Aug. 20, 2010). "Effect of injection site on in situ implant formation and drug release in vivo," J Control Release 147(3):350-358.

Pechenov, S. et al. (Apr. 16, 2004). "Injectable controlled release formulations incorporating protein crystals," J Control Release 96(1):149-158.

Perez-Marrero, R. et al. (Feb. 2004). "A subcutaneous delivery system for the extended release of leuprolide acetate for the treatment of prostate cancer," Expert Opin Pharmacother 5(2):447-457.

Perez-Merreno, R. (Nov. 2002). "A six-month, open-label study assessing a new formulation of leuprolide 7.5 mg for suppression of testosterone in patients with prostate cancer," Clinical Therapuetics 24(11):1902-1914.

Plourde, F. et al. (Nov. 28, 2005, e-published Sep. 21, 2005). "First report on the efficacy of 1-alanine-based in situ-forming implants for the long-term parenteral delivery of drugs," J Control Release 108(2-3):433-441.

Pluta, J. et al. (Dec. 20, 2006). "In vitro studies of the properties of thermosensitive systems prepared on Pluronic F-127 as vehicles for methotrexate for delivery to solid tumours," Polymers in Medicine 36(3):37-52.

QLT Inc./BC, "Form 10-K—Annual Report pursuant to Section 13 and 15(d)", (filed on Mar. 1, 2007), 436 pgs.

Rackur, H. et al. (2001). "In-Situ Forming Implants of PLGA/Leuprolide Acetate Solutions in NMP and Their in Vitro/In Vivo Release Characteristics," 28th International Symposium on Controlled Release of Bioactive Materials and Fourth Consumer Products Conference, 2001 Proceedings, Abstract 6137, pp. 884-885.

Radomsky, M.L. et al. (1993). "The Controlled Release of Ganirelix from the Atrigel™ Injectable Implant System," Proceed Intern Symp Control Rel Bioact Mater 20:458-459.

Rafienia, M. et al. (Jul. 2007). "In Vitro Evaluation of Drug Solubility and Gamma Irradiation on the Release of Betamethasone under Simulated In Vivo Conditions," Journal of Bioactive and Compatible Polymers 22:443-459.

Rathbone, M.J. et al. (Aug. 1, 2002). "Modified release drug delivery in veterinary medicine," Drug Discov Today 7(15):823-829.

Ravivarapu, H.B. et al. (Jan. 25, 2000). "Parameters affecting the efficacy of a sustained release polymeric implant of leuprolide," Int J Pharm 194(2):181-191.

Ravivarapu, H.B. et al. (Feb. 28, 2000). "Sustained activity and release of leuprolide acetate from an in situ forming polymeric implant," AAPS PharmSciTech 1(1):E1.

Reilley, K.J. et al. (Nov. 17, 2010). "Prevention of Cocaine-Conditioned Place Preference with Salvinorin a Prepared with Optimal Vehicle Conditions," 40th Annual Meeting Neuroscience 2010, Presentation Abstract, 2 pages.

Risperdal Consta Data Sheet, 2003 FDA Approved, 53 pages.

Schoenhammer, K. et al. (Apr. 17, 2009, e-published Dec. 24, 2008). "Injectable in situ forming depot systems: PEG-DAE as novel solvent for improved PLGA storage stability," Int J. Pharm 371(1-2):33-39.

Schoenhammer, K. et al. (Dec. 2009, e-published Oct. 1, 2009). "Poly(ethyleneglycol) 500 dimethylether as novel solvent for injectable in situ forming depots," Pharm Res 26(12):2568-2577.

Schulman, C.C. (2005). "LHRH Agonists in Prostate Cancer Optimising Testosterone Control with Eligard®," European Urology Supplements 4:1-3.

Schwach-Abdellaoui, K. et al. (Jul. 2000). "Local delivery of antimicrobial agents for the treatment of periodontal diseases," Eur J Pharm Biopharm 50(1):83-99.

Sherman, J.M. et al. (1994). "Localized Delivery of Bupivacaine HCL from Astrigel™ Formulations for the Management of Post-operative Pain," Pharmaceutical Research 11(10), PDD7574, 2 pages.

Sinha, V.R. et al. (Jun. 18, 2004). "Poly-epsilon-caprolactone microspheres and nanospheres: an overview," Int J. Pharm 278(1):1-23.

Smith, R.W. et al. (2004). "A Study of Water Diffusion, in Both Radial and Axial Directions, into Biodegradable Monolithic Depots Using Ion Beam Analysis," Polymer 45:4893-4908.

Southard, G.L. et al. (Feb. 1998). "Subgingival controlled release of antimicrobial agents in the treatment of periodontal disease," Int J Antimicrob Agents 9(4):239-253.

Southard, G.L. et al. (Sep. 1998). "The drug delivery and biomaterial attributes of the ATRIGEL technology in the treatment of periodontal disease," Expert Opin Investig Drugs 7(9):1483-1491.

Stroup, T. S, et al., (Apr. 2006). "Effectiveness of Olanzapine, Quetiapine, Risperidone, and Ziprasidone in Patients With Chronic Schizophrenia Following Discontinuation of a Previous Atypical Antipsychotic," Am J. Psychiatry 163(4):611-622.

Sundaram, S. et al. (2004). "Peptides: Nasal and Pulmonary Delivery of Deslorelin, a Peptide Drug," American Pharmaceutical Review 130-139.

Swanson, B.N. (Jan.-Jun. 1985). "Medical use of dimethyl sulfoxide (DMSO)," Rev Clin Basic Pharm 5(1-2):1-33.

Tipton, A.J. et al. (Oct. 1991). "A Biodegradable, Injectable Delivery System for NonSteroidal Anti-Flammatory Drugs," Pharmaceutical Research 8(10), PDD 7279, 2 pages.

Toot, J.D. et al. (2013). International Journal of Toxicology 32(1):66.

Tserki et al. ("Biodegradable aliphatic polyesters. Part II. Synthesis and characterization of chain extended poly(butylene succinate-co-butylene adipate" in Polymer Degradation and Stability 91 (2006) 377-384).

Tunn, U.W. (Jul. 29, 2011). "A 6-month depot formulation of leuprolide acetate is safe and effective in daily clinical practice: a non-interventional prospective study in 1273 patients," BMC Urology 11:15.

Wang, L. et al. (May 10, 2012, e-published Feb. 23, 2012). "Design of a long-term antipsychotic in situ forming implant and its release control method and mechanism," Int J Pharm 427(2):284-292.

Wikipedia (2016). "Risperidone," located at <https://en.wikipedia.org/w/indez.php?title=Risperidone&printable=yes>. last visited Oct. 10, 2016, 8 pages.

(56) References Cited

OTHER PUBLICATIONS

Winzenburg, G. et al. (Jun. 23, 2004). "Biodegradable polymers and their potential use in parenteral veterinary drug delivery systems," Adv Drug Deliv Rev 56(10):1453-1466.

Wischke, C. et al. (Oct. 2010, e-published Jul. 29, 2010). "Development of PLGA-based injectable delivery systems for hydrophobic fenretinide," Pharm Res 27(10):2063-2074.

Wolff, E.D. et al. (1994). "Use of Bio-Beads SM-4 Adsorbent for Bioburden Testing of Atrigel™ Biodegradable Delivery System Containing 10% Doxycycline," ASM Las Vegas 1994, Abstracts, 3 pages.

World Health Organization (2001). N-Methyl-2-Pyrrolidone, Concise International Chemical Assessment Document 35, 39 pages.

Wu, Z. et al. (Oct. 2014, e-published Jul. 1, 2014). "Thermosensitive hydrogel used in dual drug delivery system with paclitaxel-loaded micelles for in situ treatment of lung cancer," Colloids Surf B Biointerfaces 122:90-98.

Xia et al. ("Uniform biodegradable microparticle systems for controlled release" in J. Controlled Release 2002, Jul. 18; (82(1): 137-147).

Yaksh, T.L. et al. (1991). "The utility of 2-hydroxpropyl-beta-cyclodextrin as a vehicle for the intracerebral and intrathecal administration of drugs," Life Sci 48(7):623-633.

Yang, Y. et al. (May 2012, e-published Mar. 15, 2012). "Improved initial burst of estradiol organogel as long-term in situ drug delivery implant: formulation, in vitro and in vivo characterization," Drug Dev Ind Pharm 38(5):550-556.

Yehia, S.A. et al. (Jun. 2012, e-published Nov. 18, 2011). "A novel injectable in situ forming poly-DL-lactide and DL-lactide/glycolide implant containing liposheres for controlled drug delivery," J Liposome Res 22(2):128-138.

Zhu, G. et al. (2000). "Stabilization of proteins encapsulated in cylindrical poly(lactide-co-glycolide) implants: mechanism of stabilization by basic additives," Pharm Res 17(3):351-357.

SUSTAINED RELEASE SMALL MOLECULE DRUG FORMULATION

CROSS REFERENCE TO RELATED APPLICATIONS

This application is a Continuation of application Ser. No. 14/701,713 filed Apr. 30, 2015, which is a Continuation application Ser. No. 13/790,930 filed Mar. 8, 2013, which is a Continuation application Ser. No. 11/535,398, filed Sep. 26, 2006, which claims benefit of provisional Application No. 60/722,845, filed Sep. 30, 2005. The disclosures of application Ser. Nos. 14/701,173, 13/790,930 and 11/535,398 are expressly incorporated by reference herein in their entireties.

BACKGROUND OF THE INVENTION

The invention relates generally to delivery of small molecule drugs.

The term "small molecule drug," as used herein, refers to beneficial agents having low molecular weight. The beneficial agents are usually synthesized by organic chemistry, but may also be isolated from natural sources such as plants, fungi, and microbes. The common routes for delivering small molecule drugs are oral, injection, pulmonary, and transdermal.

Many psychotherapeutic drugs are small molecule drugs and are usually provided as oral pills or bolus injections that can be administered one or more times daily. However, oral pills and bolus injections may not be optimal routes for administering small molecule psychotherapeutic drugs because of the peaks and troughs observed in plasma concentration after dosing. Adverse effects and loss of therapeutic effect have been associated with plasma concentration peaks and troughs, respectively.

From the foregoing, psychotherapy as well as other forms of therapy presently relying on small molecule drugs administered in the form of oral pills and bolus injections may benefit from a sustained release dosage form designed to minimize variations in plasma concentration following dosing. Administration of psychotherapeutic agents as sustained release formulations will also increase patient compliance.

BRIEF SUMMARY OF THE INVENTION

In one aspect, the invention relates to an injectable depot formulation which comprises a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

In another aspect, the invention relates to a method of administering a small molecule drug to a subject in a controlled manner which comprises implanting in the subject an effective amount of an injectable depot formulation comprising a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

Other features and advantages of the invention will be apparent from the following description.

DETAILED DESCRIPTION OF THE INVENTION

Figure 1:
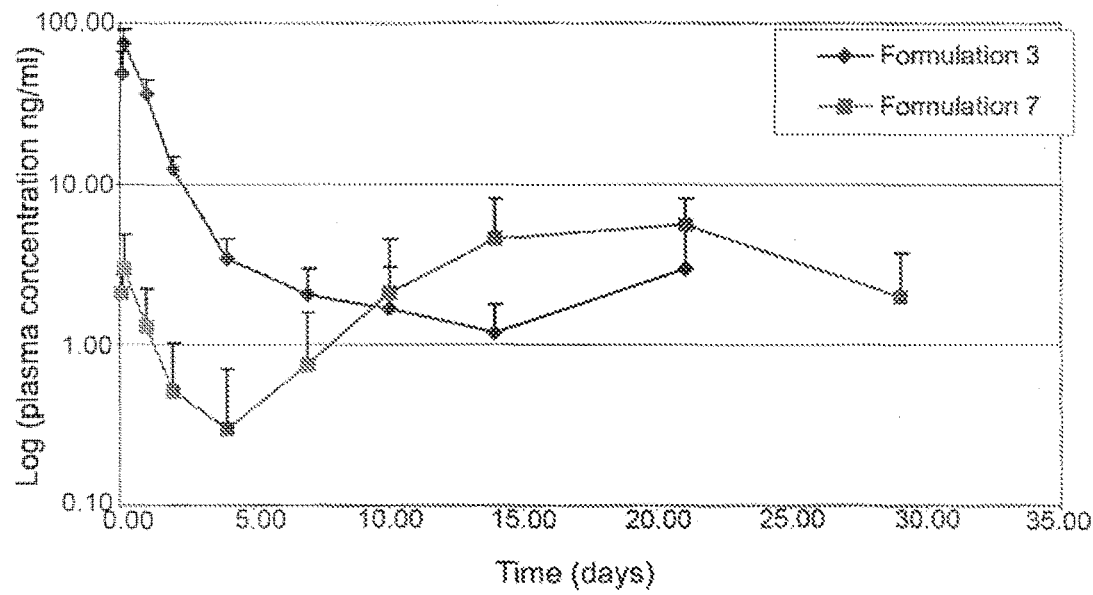
FIG. 1 shows influence of drug salt form on in vivo release profile of formulations according to embodiments of the invention.

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

The invention is based in part on the discovery that incorporation of a sparingly soluble small molecule drug in a depot gel vehicle produces a small molecule drug formulation that has near zero-order release in vivo. The release profile shows minimal lag time and burst. For a depot formulation, this release profile is surprising because the prevailing thought in the art is that a low burst, near zero-order release is virtually impossible to attain unless special steps are taken, such as coatings for drugs and microencapsulation. Several small drug formulations have been identified in this invention with in vivo release profiles having a $C_{max}$ to $C_{min}$ ratio less than 200 and lag time, $T_{lag}$, less than 0.2.

The variable "$C_{min}$" is the minimum drug concentration in plasma or serum. The variable "$C_{max}$" is the maximum drug concentration in plasma or serum. The variable "$T_{lag}$" is the ratio of $T_{valley}$ to $T_{total}$, where $T_{valley}$ is less than $T_{total}$. The variable "$T_{valley}$" is the time to reach $C_{valley}$. The variable "$C_{valley}$" is the first trough of drug concentration in plasma or serum during release. The variable "$T_{total}$" is the total release duration.

Small molecule drug formulations according to embodiments of the invention can be prepared as depot injections. The environment of use is a fluid environment and may include a subcutaneous, intramuscular, intramyocardial, adventitial, intratumoral, or intracerebral portion, a wound site, or tight joint spaces or body cavity of a human or animal. Multiple or repeated injections may be administered to the subject, for example, when the therapeutic effect of the drug has subsided or the period of time for the drug to have a therapeutic effect has lapsed or when the subject requires further administration of the drug for any reason. The formulation serves as an implanted sustained release drug delivery system after injection into the subject. Such controlled release can be over a period of one week, more than one week, one month, or more than one month. Preferably, the controlled release is over at least a period of one week, more preferably over a period of at least one month.

A small molecule drug formulation according to an embodiment of the invention includes a depot gel vehicle. The depot gel vehicle includes a biocompatible polymer, i.e., a polymer that would not cause irritation or necrosis in the environment of use. Biocompatible polymers that may be useful in the invention may be bioerodible, i.e., gradually decompose, dissolve, hydrolyze and/or erode in situ. Examples of bioerodible polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, terpolymers and mixtures thereof. The polymer is typically present in the depot gel vehicle in an amount ranging from about 5 to 80% by weight, preferably from about 20 to 70%, often from about 40 to 60% by weight.

In one embodiment, the polymer is a polylactide. A polylactide polymer is a polymer based on lactic acid or a copolymer based on lactic acid and glycolic acid. The polylactide polymer can include small amounts of other comonomers that do not substantially affect the advantageous results that can be achieved in accordance with the invention. The term "lactic acid" includes the isomers L-lactic acid, D-lactic acid, DL-lactic acid, and lactide. The term "glycolic acid" includes glycolide. The polymer may have a lactic-acid to glycolic-acid monomer ratio of from about 100:0 to 15:85, preferably from about 60:40 to 75:25, often about 50:50. The polylactide polymer has a number average molecular weight ranging from about 1,000 to about 120,000, preferably from about 5,000 to about 30,000, as determined by gel permeation chromatography. Suitable polylactide polymers are available commercially.

The depot gel vehicle further includes a biocompatible solvent which when combined with the polymer forms a viscous gel, typically exhibiting viscosity in a range from 500 poise to 200,000 poise, preferably from about 1,000 poise to 50,000 poise. The solvent used in the depot gel vehicle is typically an organic solvent and may be a single solvent or a mixture of solvents. To limit water intake by the depot gel vehicle in the environment of use, the solvent, or at least one of the components of the solvent in the case of a multi-component solvent, preferably has limited miscibility with water, e.g., less than 7% by weight, preferably less than 5% by weight, more preferably less than 3% by weight miscibility with water. Examples of suitable solvents include, but are not limited to, benzyl benzoate (BB), benzyl alcohol (BA), ethyl benzoate (EB), triacetin, and N-methyl-2-pyrrolidone (NMP). The solvent is typically present in the depot gel vehicle in an amount ranging from about 20 to 95% by weight, preferably in an amount ranging from about 30 to 80% by weight, often in an amount ranging from about 40 to 60% by weight.

A formulation according to an embodiment of the invention includes a small molecule drug dispersed or dissolved in a depot gel vehicle as described above. The term "dispersed or dissolved" is intended to encompass all means of establishing the presence of the small molecule drug in the viscous gel and includes dissolution, dispersion, suspension, and the like. Small molecule drugs used in formulations of the invention are sparingly soluble in water. In a preferred embodiment, small molecule drugs used in formulations of the invention have less than 1 mg/ml solubility in water. In one embodiment, small molecule drugs used in formulations of the invention have a molecular weight in a range from 200 to 2,000 Daltons. Small molecule drugs used in formulations of the invention may have a narrow or wide therapeutic window. However, the invention generally delivers salubrious results in terms of $C_{max}$ and toxicity control for small molecule drugs having a narrow therapeutic window. The small molecule drug is typically present in the formulation in an amount ranging from about 1 to 50% by weight, more preferably in an amount ranging from about 5 to 40% by weight, often in an amount ranging from about 10 to 30% by weight.

In one embodiment, a small molecule drug formulation includes a small molecule psychotherapeutic drug, such as a small molecule antipsychotic, dopamine receptor agonist, dopamine receptor antagonist, serotonin receptor agonist, serotonin receptor antagonist, and serotonin uptake inhibitor drug. Table 1 below shows physiochemical properties of some small molecule psychotherapeutic drugs. R209130-base has the molecular formula $C_{19}H_{20}FNO$. R209130-mandelic acid salt (R209130) has the molecular formula $C_{19}H_{20}FNO \cdot C_8H_8O_3$. R209130-tartaric acid salt (R167154) has the molecular formula $C_{19}H_{20}FNO \cdot C_4H_6O_6$. R209130 and its analogs possess putative atypical antipsychotic properties and have demonstrated antianxiety, antidepressive, and socializing effects in animal models. These characteristics may be attributed to R209130 dual antagonism of central dopamine $D_2$ receptors, serotonin $5\text{-}HT_{2A}$ and $5\text{-}HT_{2C}$ receptors, and the inhibition norepinephrine uptake. Risperidone-base has the molecular formula $C_{23}H_{27}FN_4O_2$. Risperidone-pamoate has the molecular formula $C_{23}H_{27}FN_4O_2 \cdot C_{23}H_{16}O_6$. Risperidone is a combined serotonin ($5\text{-}HT_2$) and dopamine (D2) receptor antagonist.

TABLE 1

| Property | R209130 | R167154 | R209130 base | Risperidone base | Risperidone pamoate |
|---|---|---|---|---|---|
| pKa | 9.2 | 9.2 | 9.2 | 8.2/3.1 | 8.2/3.1 |
| Solubility in H$_2$O (mg/ml) | 0.32 (pH 4.9) | 41.84 (pH 3.4) | 0.008 (pH 9.5) | 0.09 (pH 8.8) | 0.2 (pH 7.2) |
| Solubility at pH 7 (mg/ml) | 0.35 | 6.1 (pH 6.5) | 2 | 1 | 0.2 (pH 7.2) |
| Solubility in BB (µg/ml) | 58.6 at 40° C. | 10.3 at 40° C. | >200,000 | 32,000 | 50 |
| Solubility in BA (mg/ml) | 7.3 at 40° C. | 41.3 at 40° C. | >200,000 | 407 | 2.97 |
| Intrinsic dissolution rate (mg/cm$^2$ · min) | 0.054 | 3.7 | 0.7 | 0.0025 | N/A |
| LogP (C$_8$OH/pH 7 buffer) | 3.9 | 4.0 | N/A | 3.04 | N/A |

TABLE 1-continued

| Property | R209130 | R167154 | R209130 base | Risperidone base | Risperidone pamoate |
|---|---|---|---|---|---|
| Molecular weight | 449.5 | 447.5 | 297.4 | 410.5 | 798.5 |

A study was conducted to determine the PK profile of a small molecule drug delivered from a depot gel vehicle according to the invention and the influence of salt form of the drug, solvent type, polymer type, polymer molecular weight, polymer/solvent ratio, drug loading, and particle size on the PK profile.

The following examples are presented for illustration purposes and are not intended to limit the invention as otherwise described herein.

Example 1

A depot gel vehicle was prepared as follows: A HDPE container was tared on a Mettler PJ3000 top loader balance. Poly D,L-lactide-co-glycolide (PLGA), (L/G ratio of 50/50), available as RESOMER® RG 502 (PLGA-502), was weighed into the container. The container containing PLGA-502 was tared, and the corresponding solvent was added to the PLGA-502. Amounts expressed as percentages for various combinations of PLGA-502 and solvent are set forth below in Table 1A. A hybrid mixer was used to mix the PLGA-502 and solvent mixture, resulting in a clear gel-like solution of the polymer in the solvent.

TABLE 1A

| Formulation | PLGA-502 (wt %, g) | Benzyl Benzoate (wt %, g) | Benzyl Alcohol (wt %, g) |
|---|---|---|---|
| A | 50.067 | 50.044 | |
| B | 50.023 | 24.988 | 24.988 |
| C | 50.365 | 45.093 | 5.1780 |
| D | 50.139 | 37.553 | 12.560 |
| E | 50.350 | 45.193 | |

Additional depot gel vehicles were prepared with solvents, selected from benzyl benzoate (BB), benzyl alcohol (BA), ethyl benzoate (EB), ethyl hydroxide (EtOH), triacetin, and N-methyl-2-pyrrolidone (NMP), and mixtures thereof, and polymers, selected from Poly D,L-lactide, available as RESOMER® L 104, RESOMER® R 104, RESOMER® 202, RESOMER® 203, RESOMER® 206, RESOMER® 207, RESOMER® 208; PLGA, L/G ratio of 50/50, available as RESOMER® RG 502H; PLGA, L/G ratio of 50/50, available as RESOMER® RG 503; PLGA, L/G ratio of 50/50, available as RESOMER® RG 755; Poly L-lactide, molecular weight of 2000, available as RESOMER® L 206, RESOMER® L 207, RESOMER® L 209, RESOMER® L 214; Poly L-lactide-co-D,L-lactide, L/G ratio of 90/10, available as RESOMER® LR 209; PLGA, L/G ratio of 75/25, available as RESOMER® RG 752, RESOMER® RG 756, PLGA, L/G ratio of 85/15, available as RESOMER® RG 858; Poly L-lactide-co-trimethylene carbonate, L/G ratio of 70/30, available as RESOMER® LT 706, and Poly dioxanone, available as RESOMER® X210 (Boehringer Ingelheim Chemicals, Inc. Petersburg, Va.); DL-lactide/glycolide (DL), L/G ratio of 100/0, available as MEDISORB® Polymer 100 DL High, MEDISORB® Polymer 100 DL Low; DL-lactide/glycolide (DL), L/G ratio of 85/15, available as MEDISORB® Polymer 8515 DL High, MEDISORB® Polymer 8515 DL Low; DL-lactide/glycolide (DL), L/G ratio of 75/25, available as MEDISORB® Polymer 7525 DL High, MEDISORB® Polymer 7525 DL Low; DL-lactide/glycolide (DL), L/G ratio of 65/35, available as MEDISORB® Polymer 6535 DL High, MEDISORB® Polymer 6535 DL Low; DL-lactide/glycolide (DL), L/G ratio of 54/46, available as MEDISORB® Polymer 5050 DL High, MEDISORB® Polymer 5050 DL Low, MEDISORB® 5050 Polymer DL 2A(3), MEDISORB® 5050 Polymer DL 3A(3), MEDISORB® 5050 Polymer DL 4A(3) (Medisorb Technologies International L.P., Cincinnati, Ohio); and PLGA (L/G ratio of 50/50), PLGA (L/G ratio of 65/35), PLGA (L/G ratio of 75/25), PLGA (L/G ratio of 85/15), Poly D,L-lactide, Poly L-lactide, Poly glycolide, Poly ϵ-caprolactone, Poly D,L-lactide-co-caprolactone (L/C ratio of 25/75), and Poly D,L-lactide-co-caprolactone (L/C ratio of 75/25), available from Birmingham Polymers, Inc., Birmingham, Ala. Polycaprolactone-glycolic acid-lactic acid copolymer (PCL-GA-LA) was also used either mixed with polyvinylpyrrolidone (PVP) or by itself. Typical molecular weights of these polymers are in the range of 6,000 to 20,000.

Example 2

Drug particles were prepared as follows: R209130, R167154, risperidone base, or risperidone pamoate drug was passed through sieves of different sizes to obtain drug particles having a certain range of particle size distribution. Particles in the range of 20 to 63 μm, 63 to 125 μm, 75 to 125 μm, or less than 38 μm were obtained. Micronized particles received were also used as drug particles.

Example 3

Depot formulations were prepared as follows: sieved drug particles prepared as described in Example 2 were added into the depot gel vehicles prepared as described in Example 1 in an amount of 0 to 50% by weight and blended manually until the drug particles were wetted completely. Then, the mixture of drug particles and depot gel was thoroughly blended by conventional mixing using a Caframo mechanical stirrer with an attached square-tip metal spatula. Final homogeneous gel formulations were transferred to 3, 10, or 30 cc disposable syringes for storage or dispensing.

Example 4

A representative number of implantable gels were prepared in accordance with the foregoing procedures and tested in vivo in rats to determine release of the drug as determined by blood serum or plasma concentration of drug as a function of time.

In general, in vivo studies in rats were performed following an open protocol to determine plasma levels of the drug (e.g., R209130, R167154, risperidone base, risperidone pamoate) upon systemic administration of the drug via the implant systems of the invention. Depot gel formulations containing the drug, prepared as described in the Examples above, were loaded into 0.5 cc disposable syringes. Disposable needles (18 gauge) were attached to the syringes and heated to 37° C. using a circulator bath. The depot gel formulations were injected into rats. Blood was drawn at specified time intervals and analyzed for drug content. All plasma samples were stored at 4° C. prior to analysis.

Example 5

This example investigates influence of drug salt form on in vivo release of small molecule drugs from depot gel vehicles.

Particles of R209130 and R167154, in appropriate size range, were incorporated in depot gel vehicles, as per procedure in Example 3. Resulting formulations are illustrated in Table 2 below. Final homogeneous depot formulations were transferred to 3, 10, or 30 cc disposable syringes for storage or dispensing. In vivo release of the drugs were analyzed, as per procedure in Example 4. In vivo release profiles of the formulations are shown in FIG. 1. $C_{max}$ to $C_{min}$ ratio and $T_{lag}$ of the formulations are shown in Table 2. R167154 and 8209130 are different salt forms of the same drug. Formulation 7 (R209130) has $C_{max}$ to $C_{min}$ ratio of 19.2 and $T_{lag}$ of 0.61, while formulation 3 (R167154) has $C_{max}$ to $C_{min}$ ratio of 25.7 and $T_{lag}$ of 0.33. This example shows that in vivo release is influenced by salt form of the formulation. Even though $T_{lag}$ for formulation 7 (R209130) is higher than $T_{lag}$ for formulation 3 (R167154), formulation 7 appears to have better release rate profile and duration of release in comparison to formulation 3.

TABLE 2

| No. | PLGA (wt %) | BA (wt %) | BB (wt %) | Triacetin (wt %) | Drug (wt %) | $C_{max}/C_{min}$ | $T_{lag}$ |
|---|---|---|---|---|---|---|---|
| $3^{2,a,II,\alpha,A}$ | 45 | 22.5 | 22.5 | 0 | 10 | 25.7 | 0.33 |
| $7^{1,a,II,\alpha,B}$ | 45 | 22.5 | 22.5 | 0 | 10 | 19.2 | 0.61 |

[1] = R209130,
[2] = R167154,
[3] = risperidone base,
[4] = risperidone pamoate;
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
[NV] = no valley Example 6

This example investigates influence of solvent type on in vivo release of small molecule drugs from depot gel vehicles.

Figure 2:
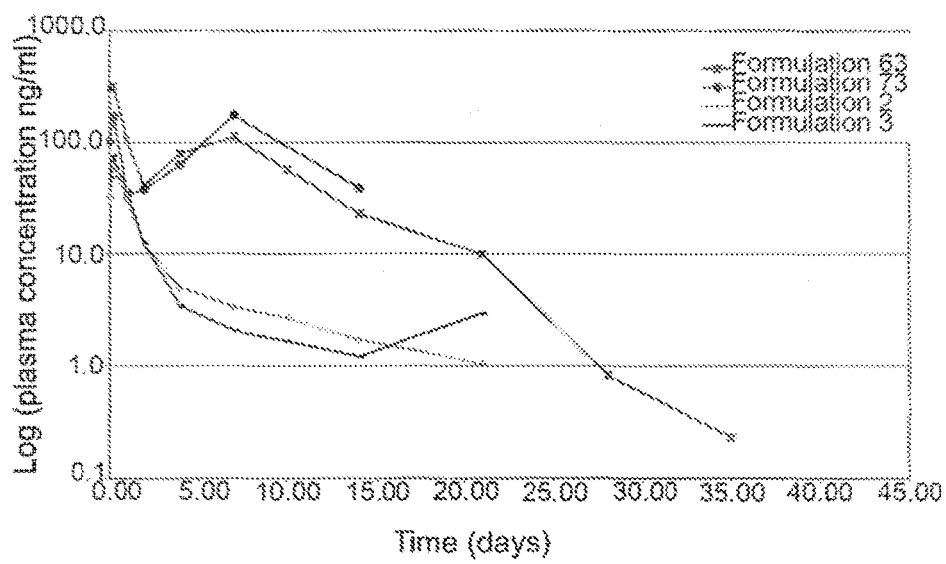
FIG. 2 shows influence of solvent type on in vivo release profile of formulations according to embodiments of the invention.

Depot gel vehicles were prepared with PLGA-502 and a solvent selected from BA, BB, EB, EtOH, NMP, and triacetin, and combinations thereof, as per procedure in Example 1. The depot gel vehicles were loaded with drug substance, in appropriate range, as per procedure in Example 3. Resulting formulations are illustrated in Table 3 below. Final homogeneous depot formulations were transferred to 3, 10 or 30 cc disposable syringes for storage or dispensing. In vivo release profiles of the formulations in Table 3 are shown in FIG. 2. $C_{max}$ to $C_{min}$ ratio and $T_{lag}$ of the formulations are shown in Table 3.

TABLE 3

| No. | Target content in formulation (% w/w) | | | | | | | | $C_{max}/C_{min}$ | $T_{lag}$ |
| | PLGA | BA | BB | EtOH | NMP | Triacetin | EB | Drug | | |
|---|---|---|---|---|---|---|---|---|---|---|
| $2^{2,a,II,\alpha,A}$ | 45 | 0 | 45 | 0 | 0 | 0 | 0 | 10 | 59.86 | NV |
| $3^{2,a,II,\alpha,A}$ | 45 | 22.5 | 22.5 | 0 | 0 | 0 | 0 | 10 | 25.68 | 0.33 |
| $10^{1,a,III,\alpha,C}$ | 40 | 40 | 0 | 0 | 0 | 0 | 0 | 20 | 4.35 | 0.61 |
| $14^{1,a,III,\alpha,C}$ | 40 | 20 | 20 | 0 | 0 | 0 | 0 | 20 | 3.15 | 0.50 |

TABLE 3-continued

| | Target content in formulation (% w/w) | | | | | | | | $C_{max}/$ | |
|---|---|---|---|---|---|---|---|---|---|---|
| No. | PLGA | BA | BB | EtOH | NMP | Triacetin | EB | Drug | $C_{min}$ | $T_{lag}$ |
| 63[3,a,VII,α,C] | 43.3 | 0 | 0 | 0 | 0 | 43.3 | 0 | 13.4 | 1364.43 | 0.14 |
| 73[3,a,VII,α,G] | 43.3 | 0 | 0 | 0 | 0 | 0 | 43.3 | 13.4 | 5.20 | N/A |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
[NV] = no valley In Table 3 above, formulation 63 (risperidone base/PLGA/triacetin depot) has a $C_{max}$ to $C_{min}$ ratio of 1364.64. On the other hand, formulation 73 (risperidone base/PLGA/EB depot) has a $C_{max}$ to $C_{min}$ ratio of 5.20, which is significantly lower than the $C_{max}$ to $C_{min}$ ratio for formulation 63. Formulation 2 (R167154/PLGA/BB depot) has a $C_{max}$ to $C_{min}$ ratio of 59.68. On the other hand, formulation 3 (R167154/PLGA/BA/BB) has a $C_{max}$ to $C_{min}$ ratio of 25.68, which is less than half the $C_{max}$ to $C_{min}$ ratio for formulation 2. This indicates that solvent type can influence in vivo release profile of the formulation.

Example 7

This example investigates influence of polymer type on in vivo release of small molecule drugs from depot gel vehicles.

Figure 3:
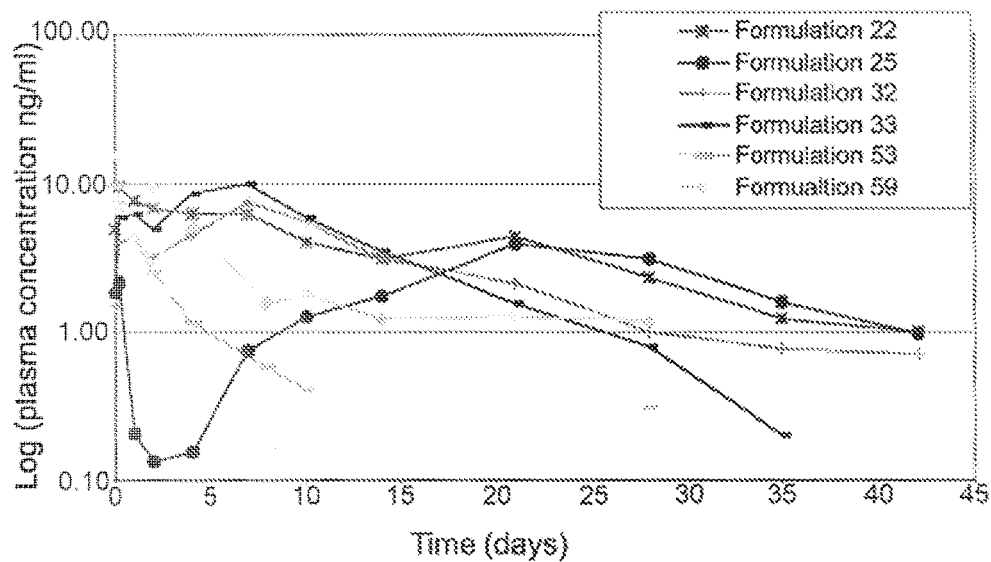
FIG. 3 shows influence of polymer type on in vivo release profile of formulations according to embodiments of the invention.

Depot gel vehicles were prepared with different polymers and loaded with R209130, in appropriate size range, as per procedure in Example 3. Resulting formulations are illustrated in Table 4 below. Final homogeneous depot formulations were transferred to 3, 10 or 30 cc disposable syringes for storage or dispensing. Table 4 shows $C_{max}$ to $C_{min}$ ratio and $T_{lag}$ for in vivo release profiles of the formulations. FIG. 3 shows in vivo release profiles of formulations in Table 4.

TABLE 4

| | Target content in formulation (% w/w) | | | | | |
|---|---|---|---|---|---|---|
| No. | Polymer | BA | BB | Drug | $C_{max}/C_{min}$ | $T_{lag}$ |
| 22[1,a,IV,α,C] | 35 | 35 | 0 | 30 | 9.86 | 0.17 |
| 23[1,a,IV,α,C] | 35 | 0 | 35 | 30 | 6.83 | 0.17 |
| 24[1,a,IV,α,E] | 35 | 0 | 35 | 30 | 44.0 | NV |
| 25[1,c,IV,α,C] | 35 | 0 | 35 | 30 | 29.49 | 0.45 |
| 32[1,d,IV,α,C] | 35 | 0 | 35 | 30 | 10.65 | 0.12 |
| 33[1,f,IV,α,C] | 35 | 0 | 35 | 30 | 6.35 | 0.14 |
| 34[1,a,IV,α,C] | 35 | 35 | 0 | 30 | 8.75 | 0.23 |
| 35[1,c,IV,α,C] | 35 | 0 | 35 | 30 | 44.21 | NV |
| 48[1,c,IV,α,E] | 35 | 0 | 35 | 30 | 163.12 | NV |
| 53[1,e,IV,α,E] | 35 | 0 | 35 | 30 | 31.16 | 0.25 |
| 59[1,d,IV,α,C] | 35 | 0 | 35 | 30 | 6.26 | 0.07 |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
NV = no valley Example 8

This example investigates influence of molecular weight of polymers on in vivo release of small molecule drugs from depot gel vehicles.

Depot gel vehicles were prepared with polymers with different molecular weights and loaded with drug substance, in appropriate size range, as per procedure in Example 3. Resulting formulations are illustrated in Table 5 below. Final homogeneous depot formulations were transferred to 3, 10 or 30 cc disposable syringes for storage or dispensing. Table 5 shows $C_{max}$ to $C_{min}$ ratio and $T_{lag}$ for in vivo release profiles of the formulations.

TABLE 5

| | Target content in Formulation (% w/w) | | | | | $C_{max}/$ | |
|---|---|---|---|---|---|---|---|
| No. | PLGA | BA | BB | Triacetin | Drug | $C_{min}$ | $T_{lag}$ |
| $10^{1,a,III,\alpha,C}$ | 40 | 40 | 0 | 0 | 20 | 4.35 | 0.61 |
| $11^{1,a,III,\alpha,D}$ | 40 | 40 | 0 | 0 | 20 | 12.06 | 0.61 |
| $12^{1,a,IV,\alpha,C}$ | 35 | 35 | 0 | 0 | 30 | 4.78 | 0.14 |
| $13^{1,a,IV,\alpha,D}$ | 35 | 35 | 0 | 0 | 30 | 5.29 | 0.36 |
| $21^{1,c,III,\alpha,C}$ | 40 | 40 | 0 | 0 | 20 | 48.55 | No valley |
| $25^{1,c,IV,\alpha,C}$ | 35 | 0 | 35 | 0 | 30 | 29.49 | 0.45 |
| $26^{1,c,IV,\alpha,D}$ | 35 | 0 | 35 | 0 | 30 | 41.67 | No valley |
| $48^{1,c,IV,\alpha,E}$ | 35 | 0 | 35 | 0 | 30 | 163.12 | No valley |
| $49^{1,c,IV,\delta,E}$ | 42 | 0 | 28 | 0 | 30 | 66.31 | 0.39 |
| $63^{3,a,VII,\alpha,C}$ | 43.3 | 0 | 0 | 43.3 | 13.4 | 1364.43 | 0.14 |
| $64^{4,c,VIII,\alpha,C}$ | 36.9 | 0 | 36.9 | 0 | 26.1 | 11.66 | No valley |
| $69^{4,a,VIII,\alpha,E}$ | 36.9 | 0 | 36.9 | 0 | 26.1 | 14.12 | 0.90 |
| $70^{4,c,VIII,\alpha,C}$ | 36.9 | 0 | 36.9 | 0 | 26.1 | 22.11 | no valley |
| $72^{3,a,VII,\alpha,G}$ | 43.3 | 0 | 43.3 | 0 | 13.4 | 24.48 | N/A |

$^1$= R209130,
$^2$= R167154,
$^3$= risperidone base,
$^4$= risperidone pamoate,
$^a$= 50/50 PLGA-502 (MW = 16,000),
$^b$= 50/50 PLGA-502H (MW = 11,000),
$^c$= 50/50 PLGA (MW = 6400),
$^d$= 40/55/5 PCL-GA-LA (MW = ~13,500),
$^e$= 75/25 PLGA (MW = 14,300),
$^f$= 80/20 PCL-GA-LA/PVP,
$^g$= RG502:RG502H (1:1);
$^\alpha$= P/S ratio of 50/50,
$^\beta$= P/S ratio of 40/60,
$^\chi$= P/S ratio of 45/55,
$^\delta$= P/S ratio of 60/40,
$^\epsilon$= P/S ratio of 55/45;
$^A$= 63-125 μm,
$^B$= 20-63 μm,
$^C$= 75-125 μm,
$^D$= <38 μm,
$^E$= micronized,
$^F$= as is,
$^G$= not applicable;
$^{NV}$= no valley Example 9

This example investigates influence of polymer/solvent ratios on in vivo release of small molecule drugs from depot gel vehicles.

Depot gel vehicles were prepared with different polymer/solvent ratios and loaded with drug substance, in appropriate size range, as per procedure in Example 3. Resulting formulations are illustrated in Table 6 below. Final homogeneous depot formulations were transferred to 3, 10 or 30 cc disposable syringes for storage or dispensing. Table 6 shows $C_{max}$ to $C_{min}$ ratio and $T_{lag}$ for in vivo release profiles of the formulations.

TABLE 6

| | Target content in Formulation (% w/w) | | | | $C_{max}/$ | |
|---|---|---|---|---|---|---|
| No. | PLGA | BB | EtOH | Drug | $C_{min}$ | $T_{lag}$ |
| $22^{1,a,IV,\alpha,C}$ | 35 | 0 | 0 | 30 | 9.86 | 0.17 |
| $23^{1,a,IV,\alpha,C}$ | 35 | 35 | 0 | 30 | 6.83 | 0.17 |

TABLE 6-continued

| | Target content in Formulation (% w/w) | | | | $C_{max}/$ | |
|---|---|---|---|---|---|---|
| No. | PLGA | BB | EtOH | Drug | $C_{min}$ | $T_{lag}$ |
| $24^{1,a,IV,\alpha,E}$ | 35 | 35 | 0 | 30 | 44.00 | NV |
| $25^{1,c,IV,\alpha,C}$ | 35 | 35 | 0 | 30 | 29.49 | 0.45 |
| $26^{1,c,IV,\alpha,D}$ | 35 | 35 | 0 | 30 | 41.67 | NV |
| $27^{1,c,IV,\beta,C}$ | 28 | 42 | 0 | 30 | 54.16 | NV |
| $28^{1,c,IV,\beta,D}$ | 28 | 42 | 0 | 30 | 120.74 | NV |
| $29^{1,a,IV,\chi,C}$ | 31.5 | 34.65 | 3.85 | 30 | 1.93 | NV |
| $30^{1,a,IV,\chi,D}$ | 31.5 | 34.65 | 3.85 | 30 | 7.07 | 0.29 |
| $48^{1,c,IV,\alpha,E}$ | 35 | 35 | 0 | 30 | 163.12 | NV |
| $49^{1,c,IV,\delta,E}$ | 42 | 28 | 0 | 30 | 66.31 | 0.39 |
| $52^{1,e,IV,\beta,E}$ | 28 | 42 | 0 | 30 | 47.86 | NV |
| $53^{1,e,IV,\alpha,E}$ | 35 | 35 | 0 | 30 | 31.16 | 0.25 |
| $56^{1,b,IV,\epsilon,F}$ | 38.5 | 31.5 | 0 | 30 | 17.10 | NV |
| $65^{4,c,VIII,\alpha,E}$ | 36.9 | 36.9 | 0 | 26.1 | 50.87 | NV |
| $66^{4,c,VIII,\epsilon,G}$ | 40.6 | 33.2 | 0 | 26.1 | 38.39 | NV |
| $67^{4,c,VIII,\epsilon,G}$ | 33.2 | 40.6 | 0 | 26.1 | 43.55 | NV |

$^1$= R209130,
$^2$= R167154,
$^3$= risperidone base,
$^4$= risperidone pamoate,
$^a$= 50/50 PLGA-502 (MW = 16,000),
$^b$= 50/50 PLGA-502H (MW = 11,000),
$^c$= 50/50 PLGA (MW = 6400),
$^d$= 40/55/5 PCL-GA-LA (MW = ~13,500),
$^e$= 75/25 PLGA (MW = 14,300),
$^f$= 80/20 PCL-GA-LA/PVP,
$^g$= RG502:RG502H (1:1);
$^\alpha$= P/S ratio of 50/50,
$^\beta$= P/S ratio of 40/60,
$^\chi$= P/S ratio of 45/55,
$^\delta$= P/S ratio of 60/40,
$^\epsilon$= P/S ratio of 55/45;
$^A$= 63-125 μm,
$^B$= 20-63 μm,
$^C$= 75-125 μm,
$^D$= <38 μm,
$^E$= micronized,
$^F$= as is,
$^G$= not applicable;
$^{NV}$= no valley Example 10

This example investigates influence of drug loading on in vivo release of small molecule drugs from depot gel vehicles Depot gel vehicles were prepared with varying percentages of drug, in appropriate size range, as per procedure in Example 3. Resulting formulations are illustrated in Table 7 below. Final homogeneous depot formulations were transferred to 3, 10 or 30 cc disposable syringes for storage or dispensing. Table 7 shows $C_{max}$ to $C_{min}$ ratio and $T_{lag}$ for in vivo release profiles of the formulations.

TABLE 7

| | Target content in Formulation (% w/w) | | | | $C_{max}/$ | |
|---|---|---|---|---|---|---|
| Formulation No. | PLGA | BA | BB | Drug | $C_{min}$ | $T_{lag}$ |
| $4^{1,a,II,\alpha,B}$ | 45 | 45 | 0 | 10 | 4.37 | 0.50 |
| $5^{1,a,III,\alpha,B}$ | 40 | 20 | 20 | 20 | 10.66 | 0.61 |
| $7^{1,a,II,\alpha,B}$ | 45 | 22.5 | 22.5 | 10 | 19.17 | 0.61 |
| $10^{1,a,III,\alpha,C}$ | 40 | 40 | 0 | 20 | 4.35 | 0.61 |
| $11^{1,a,III,\alpha,D}$ | 40 | 40 | 0 | 20 | 12.06 | 0.61 |
| $12^{1,a,IV,\alpha,C}$ | 35 | 35 | 0 | 30 | 4.78 | 0.14 |
| $13^{1,a,IV,\alpha,D}$ | 35 | 35 | 0 | 30 | 5.29 | 0.36 |
| $14^{1,a,III,\alpha,C}$ | 40 | 20 | 20 | 20 | 3.15 | 0.50 |
| $15^{1,a,III,\alpha,D}$ | 40 | 20 | 20 | 20 | 9.60 | 0.61 |
| $16^{1,a,IV,\alpha,C}$ | 35 | 17.5 | 17.5 | 30 | 7.16 | 0.61 |

TABLE 7-continued

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 17[1,a,IV,α,D] | 35 | 17.5 | 17.5 | 30 | 17.35 | 0.36 |
| 18[1,a,V,α,C] | 30 | 30 | 0 | 40 | 3.54 | 0.39 |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
[NV] = no valley

Example 11

This example investigates influence of drug particle size on in vivo release of small molecule drugs from depot gel vehicles.

Depot gel vehicles were prepared and loaded with drug particles in appropriate size range, as per procedure in Example 3. Resulting formulations are illustrated in Table 8 below. Final homogeneous depot formulations were transferred to 3, 10 or 30 cc disposable syringes for storage or dispensing. Table 8 shows $C_{max}$ to $C_{min}$ ratio and $T_{lag}$ for in vivo release profiles of the formulations.

TABLE 8

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 7[1,a,II,α,B] | 45 | 22.5 | 22.5 | 10 | 19.17 | 0.61 |
| 10[1,a,III,α,C] | 40 | 40 | 0 | 20 | 4.35 | 0.61 |
| 11[1,a,III,α,D] | 40 | 40 | 0 | 20 | 12.06 | 0.61 |
| 23[1,a,IV,α,C] | 35 | 0 | 35 | 30 | 6.83 | 0.17 |
| 24[1,a,IV,α,E] | 35 | 0 | 35 | 30 | 44.00 | NV |
| 25[1,c,IV,α,C] | 35 | 0 | 35 | 30 | 29.49 | 0.45 |
| 26[1,c,IV,α,D] | 35 | 0 | 35 | 30 | 41.67 | NV |
| 64[4,c,VIII,α,C] | 36.9 | 0 | 36.9 | 26.1 | 11.66 | NV |
| 65[4,c,VIII,α,E] | 36.9 | 0 | 36.9 | 26.1 | 50.87 | NV |

TABLE 8-continued

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 66[4,c,VIII,e,G] | 40.6 | 0 | 33.2 | 26.1 | 38.39 | NV |
| 72[3,a,VII,α,G] | 43.3 | 0 | 43.3 | 13.4 | 24.48 | N/A |

[1] = R209130,
[2] = R167154,
[3] = risperidone base,
[4] = risperidone pamoate,
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
[NV] = no valley

Example 12

Figure 4:
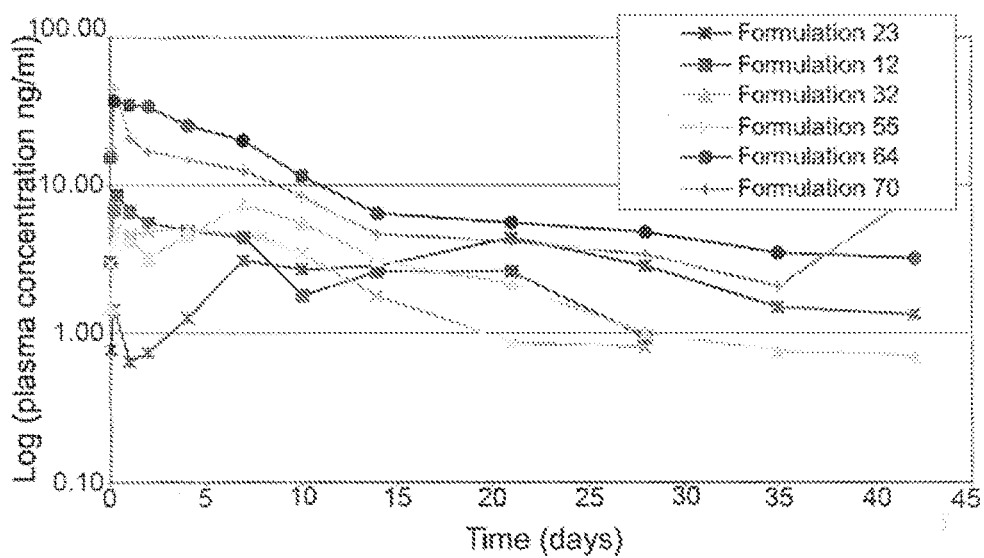
FIG. 4 shows formulations having near zero-order release profiles according to embodiments of the invention.

A formulation is described as near zero-order if the ratio of $C_{max}$ to $C_{min}$ is less than 200, preferably less than 50, more preferably less than 30. $T_{lag}$ in release of formulation is preferably less than 0.2. Formulations that do not show $C_{valley}$ do not exhibit lag. Table 9 shows a number of formulations that exhibited the characteristic near zero-order release. FIG. 4 shows in vivo release profiles of selected formulations in Table 9.

TABLE 9

| Formulation No. | Target content in Formulation (% w/w) | | | | | $C_{max}/C_{min}$ | $T_{lag}$ |
|---|---|---|---|---|---|---|---|
| | Polymer | BA | BB | EtOH | Drug Particles | | |
| 12[1,a,IV,α,C] | 35 | 35 | 0 | 0 | 30 | 4.78 | 0.14 |
| 22[1,a,IV,α,C] | 35 | 35 | 0 | 0 | 30 | 9.86 | 0.17 |
| 23[1,a,IV,α,C] | 35 | 0 | 35 | 0 | 30 | 6.83 | 0.17 |
| 29[1,a,IV,χ,C] | 31.5 | 0 | 34.65 | 3.85 | 30 | 1.93 | NV |
| 32[1,d,IV,α,C] | 35 | 35 | 0 | 0 | 30 | 10.65 | 0.12 |
| 33[1,f,IV,α,C] | 35 | 0 | 35 | 0 | 30 | 6.35 | 0.14 |
| 35[1,c,IV,α,C] | 35 | 0 | 35 | 0 | 30 | 44.21 | NV |
| 55[1,e,IV,α,C] | 35 | 0 | 35 | 0 | 30 | 6.33 | 0.11 |
| 56[1,b,IV,e,C] | 38.5 | 0 | 31.5 | 0 | 30 | 17.10 | NV |
| 60[1,c,VI,α,C] | 25 | 0 | 25 | 0 | 50 | 12.90 | 0.07 |
| 61[1,c,IV,α,C] | 35 | 0 | 35 | 0 | 30 | 26.53 | 0.11 |

TABLE 9-continued

Target content in Formulation (% w/w)

| Formulation No. | Polymer | BA | BB | EtOH | Drug Particles | $C_{max}/C_{min}$ | $T_{lag}$ |
|---|---|---|---|---|---|---|---|
| 64[4,c,VIII,α,C] | 36.9 | 0 | 36.9 | 0 | 26.1 | 11.66 | NV |
| 70[4,c,VIII,α,C] | 36.9 | 0 | 36.9 | 0 | 26.1 | 22.11 | NV |

1 = R209130,
[2] = R167154,
[3] = risperidone base,
[4] = risperidone pamoate;
[a] = 50/50 PLGA-502 (MW = 16,000),
[b] = 50/50 PLGA-502H (MW = 11,000),
[c] = 50/50 PLGA (MW = 6400),
[d] = 40/55/5 PCL-GA-LA (MW = ~13,500),
[e] = 75/25 PLGA (MW = 14,300),
[f] = 80/20 PCL-GA-LA/PVP,
[g] = RG502:RG502H (1:1);
[α] = P/S ratio of 50/50,
[β] = P/S ratio of 40/60,
[χ] = P/S ratio of 45/55,
[δ] = P/S ratio of 60/40,
[ε] = P/S ratio of 55/45;
[A] = 63-125 μm,
[B] = 20-63 μm,
[C] = 75-125 μm,
[D] = <38 μm,
[E] = micronized,
[F] = as is,
[G] = not applicable;
[NV] = no valley While the invention has been described with respect to a limited number of embodiments, those skilled in the art, having benefit of this disclosure, will appreciate that other embodiments can be devised which do not depart from the scope of the invention as disclosed herein.

What is claimed is:

1. A method of administering risperidone base to a subject, comprising:
    implanting in the subject a formulation comprising:
    a copolymer of lactic acid and glycolic acid having a number average molecular weight ranging from 1000 Daltons to 30,000 Daltons;
    an organic solvent combined with the copolymer to form a viscous gel, the organic solvent comprising N-methyl-2-pyrrolidone; and
    risperidone base in particle form incorporated in the viscous gel,
    wherein the copolymer and the N-methyl-pyrrolidone comprise a vehicle, the copolymer is present in the vehicle in an amount ranging from 40% to 55% by weight, and the organic solvent is present in the vehicle in an amount ranging from 45% to 60% by weight.

2. The method of claim 1, wherein the copolymer of lactic acid and glycolic acid has a monomer ratio of lactic acid to glycolic acid ranging from about 100:0 to 60:40.

3. The method of claim 1, wherein the copolymer of lactic acid and glycolic acid has a monomer ratio of lactic acid to glycolic acid ranging from 100:0 to 75:25.

4. The method of claim 1, wherein the copolymer has a number average molecular weight ranging from 5000 Daltons to 30,000 Daltons.

5. The method of claim 1, wherein the organic solvent consists of N-methyl-2-pyrrolidone.

6. The method of claim 1, wherein the risperidone base is present in the formulation in an amount ranging from 5 wt % to 40 wt %.

7. The method of claim 1, wherein the risperidone base is present in the formulation in an amount ranging from 10 wt % to 30 wt %.

8. The method of claim 1, wherein the copolymer of lactic acid and glycolic acid has a monomer ratio of lactic acid to glycolic acid ranging from about 100:0 to 60:40, and the copolymer has a number average molecular weight ranging from 5000 Daltons to 30,000 Daltons.

9. The method of claim 1, wherein the copolymer of lactic acid and glycolic acid has a monomer ratio of lactic acid to glycolic acid ranging from 100:0 to 75:25, and the copolymer has a number average molecular weight ranging from 5000 Daltons to 30,000 Daltons.

10. The method of claim 1, wherein the copolymer of lactic acid and glycolic acid has a monomer ratio of lactic acid to glycolic acid ranging from about 100:0 to 60:40, and the organic solvent consists of N-methyl-2-pyrrolidone.

11. The method of claim 1, wherein the copolymer of lactic acid and glycolic acid has a monomer ratio of lactic acid to glycolic acid ranging from 100:0 to 75:25, the copolymer has a number average molecular weight ranging from 5000 Daltons to 30,000 Daltons, and the organic solvent consists of N-methyl-2-pyrrolidone.

12. The method of claim 1, wherein the organic solvent consists of N-methyl-2-pyrrolidone, and the risperidone base is present in the formulation in an amount ranging from 10 wt % to 30 wt %.

13. The method of claim 1, wherein the copolymer of lactic acid and glycolic acid has a monomer ratio of lactic acid to glycolic acid ranging from about 100:0 to 60:40, the organic solvent consists of N-methyl-2-pyrrolidone, and the risperidone base is present in the formulation in an amount ranging from 10 wt % to 30 wt %.

14. The method of claim 1, wherein the copolymer of lactic acid and glycolic acid has a monomer ratio of lactic acid to glycolic acid ranging from 100:0 to 75:25, the copolymer has a number average molecular weight ranging from 5000 Daltons to 30,000 Daltons, the organic solvent consists of N-methyl-2-pyrrolidone, and the risperidone base is present in the formulation in an amount ranging from 10 wt % to 30 wt %.

15. The method of claim 1, wherein the copolymer of lactic acid and glycolic acid has a monomer ratio of lactic acid to glycolic acid ranging from 100:0 to 75:25, the organic solvent consists of N-methyl-2-pyrrolidone, and the risperidone base is present in the formulation in an amount ranging from 10 wt % to 30 wt %.

16. The method of claim 1, wherein the formulation exhibits a lag time less than 0.2.

17. The method of claim 1, wherein the risperidone base in particle form comprises particles having an average particle size ranging from 0.1 μm to 125 μm.

18. The method of claim 1, wherein the risperidone base is released from the formulation for one week.

19. The method of claim 1, wherein the risperidone base is released from the formulation for one month.

20. The method of claim 1, wherein the risperidone base in particle form comprises particles having a particle size less than 38 μm.

* * * * *